(12) United States Patent
Kawakita

(10) Patent No.: US 8,951,297 B2
(45) Date of Patent: Feb. 10, 2015

(54) STENT DELIVERY SYSTEM

(75) Inventor: Taisei Kawakita, Fujinomiya (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 400 days.

(21) Appl. No.: 13/536,220

(22) Filed: Jun. 28, 2012

(65) Prior Publication Data

US 2012/0296409 A1     Nov. 22, 2012

Related U.S. Application Data

(63) Continuation of application No. PCT/JP2010/072254, filed on Dec. 10, 2010.

(30) Foreign Application Priority Data

Dec. 28, 2009  (JP) .................................. 2009-298539

(51) Int. Cl.
*A61F 2/966* (2013.01)
*A61F 2/915* (2013.01)
*A61F 2/95* (2013.01)

(52) U.S. Cl.
CPC ................. *A61F 2/966* (2013.01); *A61F 2/915* (2013.01); *A61F 2002/91575* (2013.01); *A61F 2002/9517* (2013.01)
USPC .......................................................... 623/1.11

(58) Field of Classification Search
USPC ................. 606/108; 623/1.11, 1.12, 1.23
See application file for complete search history.

(56) References Cited

U.S. PATENT DOCUMENTS

| | | | |
|---|---|---|---|
| 7,022,133 | B2 | 4/2006 | Yee et al. |
| 7,815,669 | B2 | 10/2010 | Matsuoka et al. |
| 2006/0259124 | A1 | 11/2006 | Matsuoka et al. |

FOREIGN PATENT DOCUMENTS

| | | |
|---|---|---|
| JP | 2001-522694 A | 11/2001 |
| JP | 2007-97620 A | 4/2007 |

OTHER PUBLICATIONS

International Search Report (PCT/ISA/210) issued on Jan. 18, 2011, by the Japanese Patent Office as the International Searching Authority for International Application No. PCT/JP2010/072254.

*Primary Examiner* — Ryan Severson
(74) *Attorney, Agent, or Firm* — Buchanan Ingersoll & Rooney PC

(57) ABSTRACT

A stent delivery system is provided with a stent which, when inserted into an organism, is compressed in the center axis direction and which, when placed in the organism, can be expanded outward and restored to the shape which the stent has before being compressed; an inner tube body (inner tube); and a stent housing tube body (sheath) in which the stent is housed. The stent can be discharged by moving the stent housing tube body to the proximal side relative to the inner tube body. At least a portion of an inner surface of the stent housing tube body is a substantially polygonal prism-shaped inner surface which extends in the axial direction of the stent housing tube body.

20 Claims, 21 Drawing Sheets

STENT DELIVERY SYSTEM

CROSS REFERENCE TO RELATED APPLICATION

This application is a continuation of International Application PCT/JP2010/072254 filed on Dec. 10, 2010, which claims priority to Japanese Patent Application No. JP2009-298539, filed on Dec. 28, 2009, the entire content of which is incorporated herein by reference.

TECHNICAL FIELD

This invention relates to a stent delivery system for indwelling a stent at a stenosis or occlusion formed in a living body such as blood vessel, bile duct, trachea, esophagus, urethra, digestive tract, and other organs.

BACKGROUND DISCUSSION

Conventionally, there have been proposed stent delivery systems to indwell a stent at a stenosis or occlusion formed in a living body lumen or body cavity such as blood vessel, bile duct, esophagus, trachea, urethra, digestive tract, and other organs to secure the lumen or body cavity space.

In the above-described stent delivery system, there are both a balloon-expandable stent and a self-expandable stent that can be used depending on the functions and the indwelling method.

In the balloon-expandable stent, the stent itself does not have the expansion function. To indwell the stent at a target part, for example, the stent, mounted on a balloon, is inserted into the target part and thereafter the balloon is inflated to expand (plastically deform) the stent by the inflation force of the balloon. This causes the stent to be brought into tight contact with the inner surface of the target part and fixed.

This type of stent needs the above-described stent dilation operation performed by the balloon. However, since it is possible to indwell the stent by attaching the stent directly to the deflated balloon, there is no large problem regarding the indwelling.

In contrast, in the self-expandable stent, the stent itself has the contraction and expansion function. To indwell this stent at a target part, the stent is inserted into the target part in the contracted state and, thereafter, the stress applied to keep the contracted (or compressed) state is removed. For example, the contracted stent is housed in a sheath having an outer diameter smaller than the inner diameter of the target part and the distal end of this sheath is made to reach the target part. Thereafter, the stent is pushed out from the sheath. The stress load is removed from the stent when it is pushed out due to the release from the sheath, and the stent is thereby expanded and restored to the shape before the contraction. This causes the stent to be brought into tight contact with the inner surface of the target part and fixed.

This type of stent does not need an expansion operation like that for the balloon-expandable stent because the stent itself has the expansion force. In addition, it is free from the problem of the diameter of the stent gradually becoming smaller due to the pressure of a blood vessel or the like and a restenosis thus occurring.

However, the self-expandable stent is generally thought to be more difficult to accurately indwell at the target part than the balloon-expandable stent. This is because, in the balloon-expandable stent, a liquid is merely injected into the balloon after the stent is disposed at the target stenosis. Therefore, the stent does not move forward or backward in the expansion of the stent. On the other hand, in the structure of the delivery system for the self-expandable stent, the stent is housed and restrained between an inner tube and an outer tube and a locking part to restrict the movement of the stent is provided on the stent proximal side of the inner tube. By pulling the outer tube toward the proximal side, the restraint of the stent is released to make the stent be self-expanded. The stent readily moves forward when being expanded which is believed to be due to looseness of the outer tube within the body cavity, or friction between the outer tube and the body cavity or the catheter into which the outer tube is introduced, or friction between the outer tube and a valve of a device called an introducer for introducing the system into the body.

An example of a self-expandable stent delivery system is shown in U.S. Pat. No. 7,815,669 (Japanese Laid-Open Patent No. 2007-97620.

This stent delivery system 1 includes a distal-side tube 2 having a guidewire lumen 21, a proximal-side tube 4 fixed to the proximal portion of the distal-side tube 2, a stent housing tubular member 5 that envelops the distal side of the distal-side tube 2 and is slidable in the proximal direction, a stent 3 housed in the tubular member 5, and a pulling wire 6 for moving the tubular member 5 toward the proximal side. The distal-side tube 2 has a proximal-side opening 23 opened on the proximal side of the distal-side tube 2, a stent locking part 22 that restricts the movement of the stent toward the proximal side, and an operation section including a pulling wire winding-up mechanism and a mechanism to restrict the amount of wire winding-up.

Furthermore, this stent delivery system 1 includes an intermediate tube 7 that encloses the proximal side of the distal-side tube 2 and the proximal side of the stent housing tubular member 5 and that is fixed to the proximal portion of the distal-side tube 2 and the distal portion of the proximal-side tube 4 at its proximal part. The intermediate tube 7 encloses the proximal side of the distal side tube 2 and the proximal side of the stent housing tubular member 5 without restricting the movement of the stent housing tubular member 5 toward the proximal side. One end of the pulling wire 6 is fixed to the stent housing tubular member 5 in the intermediate tube 7. The pulling wire 6 passes between the intermediate tube 7 and the distal-side tube 2 and extends into the proximal-side tube 4.

In this stent delivery system, the proximal-side opening of the guidewire lumen exists not at the proximal end of the system (operation section) but at the proximal end of the distal-side tube. Therefore, in a stent indwelling operation, the operation of exchanging from one delivery system to another stent delivery system is easy. Furthermore, the stent can be discharged by pulling the pulling wire toward the proximal side. Thus, the positional movement of the stent in the stent discharge operation is extremely little.

Although the system of U.S. Pat. No. 7,815,669 is sufficiently effective, it is preferable that the stent discharge operation be easier. In the system of U.S. Pat. No. 7,815,669, the compressed self-expandable stent is in contact with the inner surface of the stent housing tubular member across substantially the entirety of its outer surface. Therefore, in the stent discharge operation, substantially the entire outer surface of the compressed self-expandable stent is in sliding contact with the inner surface of the stent housing tubular member.

Accordingly, it would be desirable to decrease the contact area between the outer surface of the compressed self-expandable stent and the inner surface of the tube body that houses the stent and thereby reduce the sliding contact resistance between the outer surface of the compressed self-expandable stent and the stent housing tube body in the stent discharge operation, to thereby provide a stent delivery system in which the stent discharge operation is made easier.

SUMMARY

The stent delivery system disclosed herein includes a stent formed into a substantially cylindrical shape, an inner tube body having a guidewire lumen, and a stent housing tube body that houses the stent in a distal portion. The stent is compressed in the center axis direction when being inserted into a living body and is capable of being expanded outward to be restored to a shape before compression when being indwelled in a living body. The stent is so disposed as to cover a distal portion of the inner tube body. The stent can be discharged by moving the stent housing tube body toward the proximal side relative to the inner tube body. Moreover, in the stent delivery system disclosed herein, the inner surface of the stent housing tube body from at least the distal end of the stent housing tube body to the proximal part of the stent housing portion is a substantially polygonal prism inner surface extending along the axial direction of the stent housing tube body.

DETAILED DESCRIPTION

A stent delivery system will be described below by reference to the embodiments disclosed here as example and as shown in the accompanying drawings.

The stent delivery system (in other words, living organ lesion improving instrument) 1 includes a stent 3 formed into a substantially cylindrical shape, an inner tube body (in this embodiment, inner tube) 4 having a guidewire lumen, and a stent housing tube body (in this embodiment, sheath) 2 that houses the stent 3 in the distal portion. The stent 3 is compressed (contracted) in the center axis direction when being inserted into a living body and is capable of being expanded outward to be restored to the original shape before the compression (contraction) when being indwelled in the living body. Furthermore, the stent 3 is so disposed as to cover the distal portion of the inner tube body (inner tube) 4 and the stent 3 can be exposed (can be discharged) by moving the stent housing tube body (sheath) 2 toward the proximal side relative to the inner tube body (inner tube) 4. Moreover, an inner surface 23 of the stent housing tube body (sheath) 2, from at least the distal end of the stent housing tube body 2 to the proximal part of a stent housing portion 22, is a substantially polygonal prism inner surface extending along the axial direction of the stent housing tube body (sheath) 2.

Figure 1:
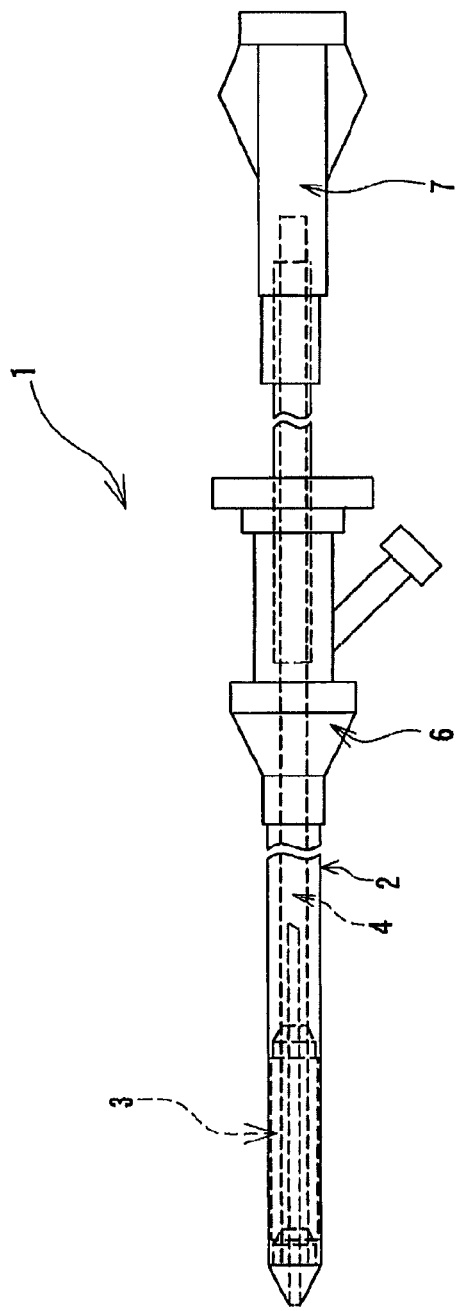
FIG. 1 is a partially omitted front view of a stent delivery system according to one embodiment disclosed here by way of example.

As shown in FIG. 1, the stent delivery system 1 of this embodiment includes the stent housing tube body (sheath) 2, the self-expandable stent 3, and the inner tube body (inner tube) 4.

As shown in FIGS. 1-4, the sheath 2 is a tubular body and both the distal end and proximal end thereof are opened. The distal-end opening functions as a discharge port of the stent 3 when the stent 3 is indwelled at a stenosis in a body cavity. The stent 3 is pushed out from this distal-end opening and thereby stress load is released, so that the stent 3 is expanded and restored to the shape before the compression. The distal portion of the sheath 2 is a stent housing portion 22 which houses the stent 3 inside.

Figure 3:
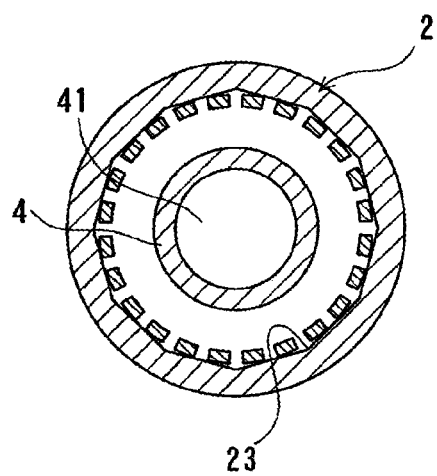
FIG. 3 is an enlarged cross-sectional view generally of the distal portion of the stent delivery system shown in FIG. 1.
Figure 4:
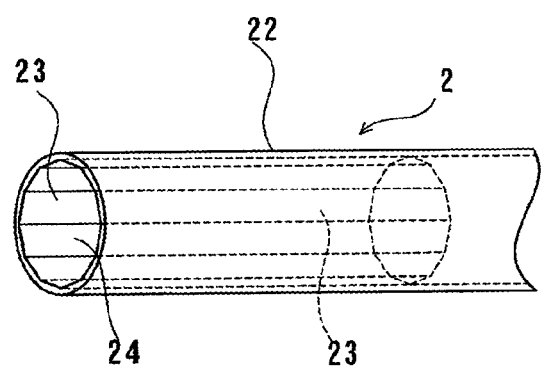
FIG. 4 is an explanatory diagram for explaining the distal portion of a stent housing tube body used in the stent delivery system disclosed here.

In the sheath 2, as shown in FIG. 3 and FIG. 4, the inner surface 23, from the distal end of the sheath 2 to the proximal part of the stent housing portion 22, is a substantially polygonal prism inner surface extending along the axial direction of the sheath 2. This substantially polygonal prism inner surface 23 may further extend toward the proximal side beyond the proximal end of the stent housing portion 22. It is preferable that the substantially polygonal prism inner surface 23 extends along the axial direction of the sheath 2 and has substantially no bent part. In particular, in the sheath 2 of the embodiment shown in FIG. 4, the substantially polygonal prism inner surface 23 is a polygonal prism inner surface extending in parallel to the axial direction (center axis) of the sheath 2. Therefore, each inner surface portion 24 forming the polygonal prism inner surface extends in parallel to the axial direction (center axis) of the sheath 2.

Thus, the contact part between the outer surface of the compressed self-expandable stent and the inner surface of the tube body that houses the stent is small and the sliding contact resistance between the outer surface of the compressed self-expandable stent and the stent housing tube body is also low in stent discharge operation. This makes the stent discharge operation easy.

Figure 5:
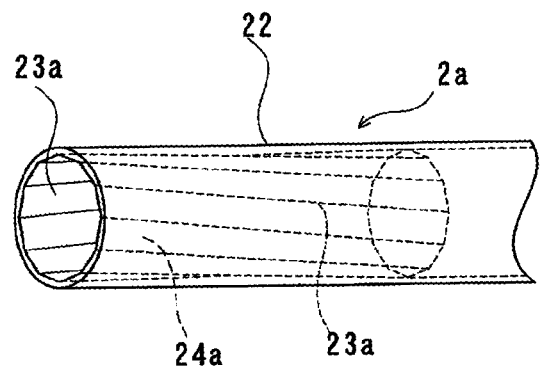
FIG. 5 is an explanatory diagram for explaining the distal portion of the stent housing tube body of another example used in the stent delivery system disclosed here.

Furthermore, in a sheath 2a, as shown by way of example in FIG. 5, the substantially polygonal prism inner surface may extend in a helical manner (preferably, a gentle helical manner) with respect to the axial direction (center axis) of the sheath 2a. In the sheath 2a of this example, each inner surface portion 24a of the substantially polygonal prism inner surface 23a extends in a helical manner (preferably, gentle helical manner) with respect to the axial direction (center axis) of the sheath 2a.

Figure 27:
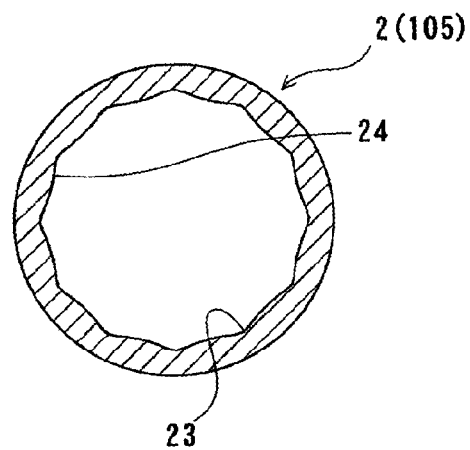
FIG. 27 is an explanatory diagram for explaining the distal portion of the stent housing tube body of a further example used in the stent delivery system disclosed here.

Moreover, in all of the above-described embodiments, each inner surface portion 24 of the substantially polygonal prism inner surface 23 may include a center part that bulges toward the inside of the sheath 2 as shown in FIG. 27. This can further decrease the contact area with the outer surface of the stent 3. It is preferable that the bulge part of each inner surface portion have no bent part and the center part of each inner surface portion slightly bulge. Furthermore, it is preferable that this bulge part is formed along the total length of each inner surface portion. In addition, this bulge part extends in parallel to the axial direction (center axis) of the sheath 2. The bulge part may correspond to the shape of each inner surface portion and extends in a helical manner (preferably, gentle helical manner) with respect to the axial direction (center axis) of the sheath 2.

Furthermore, in all of the above-described embodiments, it is preferable that the substantially polygonal prism inner surface have a regular polygon. However, it may have a polygon in which the respective sides (circumferential widths of the respective inner surface portions) are not identical. In addition, it is preferable that the substantially polygonal prism inner surface have 6 to 24 inner surface portions (the number of corners where the angled inner surfaces portions intersect), and more particularly, 8 to 12 is preferable. Furthermore, it is preferable that the respective inner surface portions of the substantially polygonal prism inner surface have a circumferential width of 0.1 to 1.3 mm, and more particularly, 0.3 to 1.0 mm.

The sheath 2 preferably has an outer diameter of 1.1 to 4.0 mm, and more particularly, 1.5 to 3.0 mm. Furthermore, the sheath 2 has a preferred inner diameter of 1.0 to 2.5 mm and a preferred length of 300 to 2500 mm, more particularly 300 to 2000 mm.

A polyolefin such as polyethylene and polypropylene, nylon, polyethylene terephthalate, fluorine-based polymer such as PTFE and ETFE, and thermoplastic elastomer are preferable as the forming material of the sheath 2 in consideration of the properties required for the sheath (flexibility, hardness, strength, slidability, kink resistance, stretch property). As the thermoplastic elastomer, an elastomer is arbitrarily selected from nylon series (e.g. polyamide elastomer), urethane series (e.g. polyurethane elastomer), polyester series (e.g. polyethylene terephthalate elastomer), and olefin series (e.g. polyethylene elastomer, polypropylene elastomer).

Moreover, it is preferable to subject the outer surface of the sheath 2 to treatment for making the outer surface assume a lubricating ability. Examples of such treatment include applying a coating or fixing thereto, a hydrophilic polymer such as poly(2-hydroxyethyl methacrylate), poly(hydroxyethyl acrylate), hydroxypropyl cellulose, methyl vinyl ether maleic anhydride copolymer, polyethylene glycol, polyacrylamide, polyvinylpyrrolidone, and dimethylacrylamide-glycidyl methacrylate copolymer. Furthermore, the above-described material may be applied as a coating or fixed on the inner surface of the sheath 2 in order to improve its capability of sliding on the stent 3 and the inner tube 4.

Figure 6:
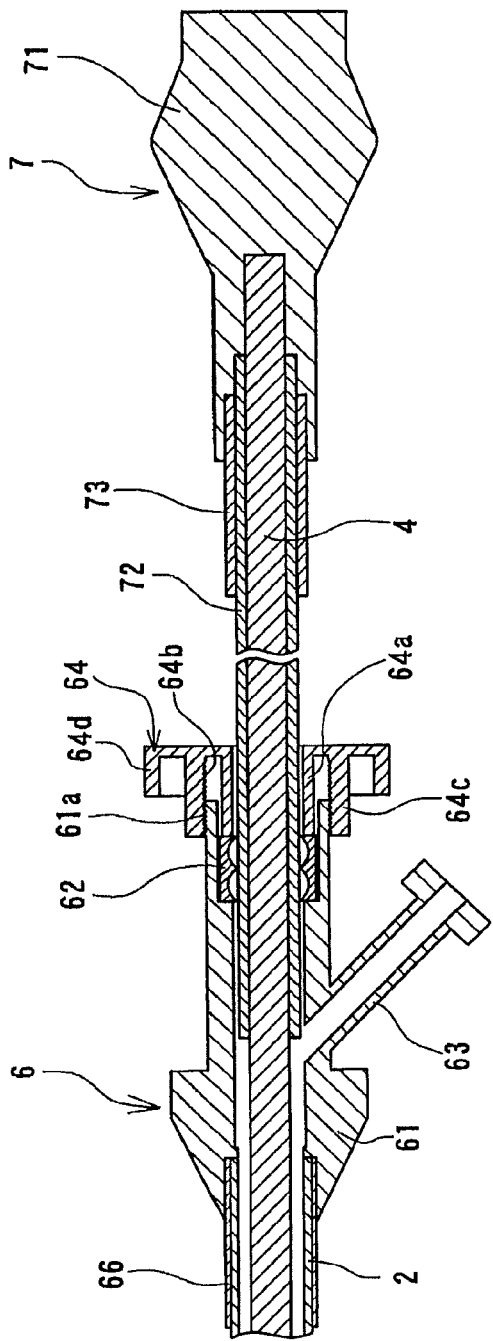
FIG. 6 is a partially omitted enlarged sectional view in the vicinity of the proximal portion of the stent delivery system shown in FIG. 1.

Furthermore, as shown in FIG. 1 and FIG. 6, a sheath hub 6 is fixed to the proximal portion of the sheath 2. As shown in FIG. 6, the sheath hub 6 has a sheath hub main body 61 and a valve body 62 that is housed in the sheath hub main body 61 and slidably holds the inner tube 4 in a liquid-tight manner. In addition, the sheath hub 6 has a side port 63 branched obliquely backward from the vicinity of the center of the sheath hub main body 61.

Moreover, the sheath hub 6 has an inner tube lock mechanism to restrict the movement of the inner tube 4. In this embodiment, the lock mechanism is configured by the valve body 62 that sandwiches the proximal portion of the inner tube 4 in a liquid-tight manner through compression, an operation member 64 to compress the valve body 62, and the sheath hub main body 61. Due to the presence of such a lock mechanism, the inner tube 4 can be fixed at an arbitrary position relative to the sheath 2. The valve body 62 is disposed in a valve body housing recess provided at the proximal portion of the sheath hub main body 61. An inner tube insertion pathway is formed inside the valve body 62 thereby forming part of a lumen for the inner tube. Furthermore, the valve body housing recess is fabricated so that its inner diameter is slightly larger than the outer diameter of the valve body 62. This enables enlargement of the diameter of the valve body in the inside direction when the valve body 62 is compressed by the operation member 64. The inside shape of the valve body 62 (in other words, the shape of the inner tube insertion pathway) is fabricated into a shape such that two substantially spherical shapes partially overlap each other in the axial direction and the diameter of the valve body 62 is decreased at both ends and the center part.

The operation member 64 has a tubular valve body pressing part 64a that protrudes toward the distal side at the center part, an inner cylinder part 64c that is formed so as to enclose this valve body pressing part 64a, and a tubular grasp part 64d that is formed so as to enclose the inner cylinder part 64c. The inner cylinder part 64c has a screw fitting part 64b capable of being screwed to a screw fitting part 61a formed on the outer surface of the proximal end of the sheath hub main body 61. The grasp part 64d is a portion for being grasped when the operation member 64 is rotated. Furthermore, inside the operation member 64, specifically inside the valve body pressing part 64a, an inside pathway is formed, thereby forming part of the lumen for the inner tube. In addition, the distal-side part of the valve body pressing part 64a enters the inside of the valve body housing recess as shown in FIG. 6.

This enables compression of the valve body 62 through the movement of the operation member 64 toward the distal end.

With the lock mechanism of this embodiment, when the operation member 64 is rotated to progress the screwing so that the operation member 64 may move toward the distal side of the sheath hub 6, the distal end of the valve body pressing part 64a comes into contact with the proximal end of the valve body 62. When the operation member 64 is further rotated to progress the screwing, the valve body 62 is compressed in the axial direction. Then, the inner diameter of the inside pathway of the valve body 62 becomes smaller along with the progression of the compression thereof and finally the inner tube 4 is grasped and fixed by the valve body 62. The lock mechanism is released by rotational operation opposite to the above-described operation.

A hard or semi-hard material is preferably used to form the sheath hub main body 61 and the operation member 64. The hard or semi-hard material may include, for example, the following materials that can be used: synthetic resin such as polycarbonate, polyolefin (e.g. polyethylene, polypropylene, ethylene-propylene copolymer), styrene-based resin [e.g. polystyrene, MS resin (methacrylate-styrene copolymer), MBS resin (methacrylate-butylene-styrene copolymer)], or polyester, and metal such as stainless steel, aluminum, or aluminum alloy.

Furthermore, an elastic material is used as the constituent material of the valve body 62. The elastic material may include, for example, one of the following rubber materials that can be used: synthetic rubber such as urethane rubber, silicone rubber, and butadiene rubber; and natural rubber such as latex rubber. In addition, e.g. the following synthetic resin elastomers are used: olefin-based elastomer (e.g. polyethylene elastomer, polypropylene elastomer), polyamide elastomer, styrene-based elastomer (e.g. styrene-butadiene-styrene copolymer, styrene-isoprene-styrene copolymer, styrene-ethylenebutylene-styrene copolymer), polyurethane, urethane-based elastomer, and fluorine resin-based elastomer.

Furthermore, a reinforcement tube 66 extending beyond the distal end of the sheath hub 6 toward the distal side is provided between the proximal portion of the sheath 2 and the sheath hub 6. This reinforcement tube 66 prevents the kink of the sheath 2 at the distal end of the sheath hub 6. It is preferable to use a heat-shrinkable tube as the reinforcement tube 66.

As shown in FIGS. 1-3 and FIG. 6, the inner tube 4 has a shaft-like inner tube main body 40, a distal portion 47 that is provided at the distal end of the inner tube main body 40 and protrudes beyond the distal end of the sheath 2, and an inner tube hub 7 fixed to the proximal portion of the inner tube main body 40.

Figure 2:
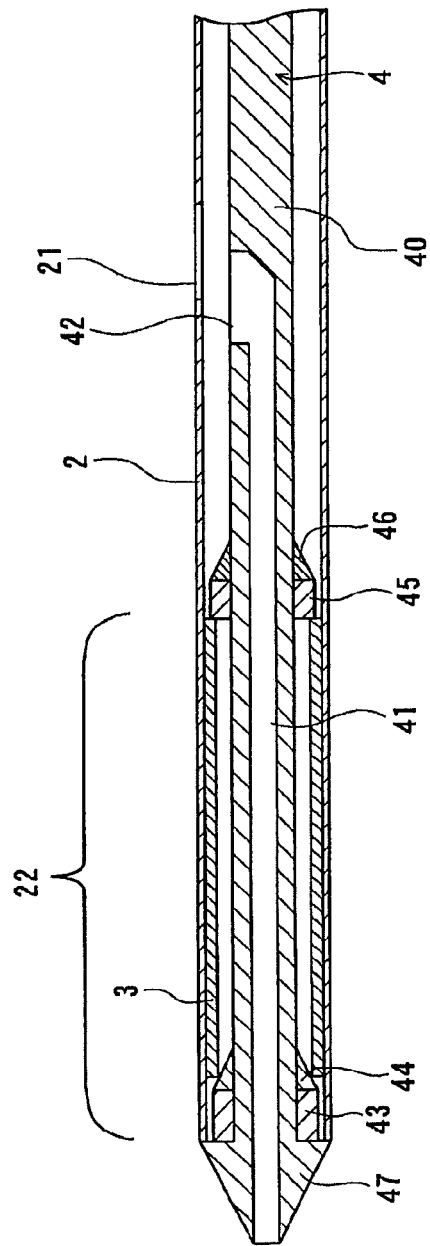
FIG. 2 is an enlarged longitudinal sectional view generally of the distal portion of the stent delivery system shown in FIG. 1.

It is preferable that the distal portion 47 protrudes beyond the distal end of the sheath 2 and be formed into a tapered shape in which the diameter is gradually reduced toward the distal end as shown in FIG. 2. Forming the distal portion 47 in this manner facilitates insertion into a stenosis. Furthermore, it is preferable for the inner tube 4 to have a stopper that is provided toward the distal end relative to the stent 3 and restricts the movement of the sheath in the distal direction. The proximal end of the distal portion 47 can abut on the distal end of the sheath 2 and functions as the above-described stopper.

It is preferable that the outer diameter of the most distal end of the distal portion 47 is 0.5 to 1.8 mm. Furthermore, it is preferable that the outer diameter of the largest diameter part of the distal portion 47 is 0.8 to 4.0 mm. Moreover, it is preferable that the length of the tapered part is 2.0 to 20.0 mm.

Furthermore, as shown in FIG. 2, the inner tube 4 has two protrusions 43 and 45 for holding the self-expandable stent 3 to be described later. It is preferable that the protrusions 43 and 45 are annular protrusions. The stent holding protrusion 43 is provided on the proximal side relative to the distal portion 47 of the inner tube 4. Furthermore, the stent pushing-out protrusion 45 is provided toward the proximal end relative to the stent holding protrusion 43 by a predetermined distance. The stent 3 is disposed between these two protrusions 43 and 45. Thus, the portion between these two protrusions 43 and 45 in the stent delivery system 1 is the stent housing portion 22. In other words, the inner tube 4 has the stent pushing-out protrusion 45 provided toward the proximal end relative to the stent housing portion 22 and the stent holding protrusion 43 provided toward the distal end relative to the stent housing portion 22. The outer diameter of these protrusions 43 and 45 is configured such that they can abut on the compressed stent 3, as described in greater detail below. Therefore, the movement of the stent 3 toward the distal side is restricted by the protrusion 43 and the movement thereof toward the proximal side is restricted by the protrusion 45. Moreover, when the sheath 2 moves toward the proximal side, the stent 3 is pushed toward the distal side by the protrusion 45 to be discharged from the sheath 2. Furthermore, it is preferable that the proximal side of the stent pushing-out protrusion 45 is defined by a tapered part 46 in which the diameter is gradually reduced toward the proximal side as shown in FIG. 2. Similarly, it is preferable that the proximal side of the stent holding protrusion 43 is defined by a tapered part 44 in which the diameter is gradually reduced toward the proximal side as shown in FIG. 2. This makes it possible to prevent the protrusion from getting stuck on the distal end of the sheath when the inner tube 4 is housed in the sheath 2 again after the inner tube 4 is exposed beyond the distal end of the sheath 2 and the stent 3 is discharged from the sheath.

It is preferable that the outer diameter of each of the protrusions 43 and 45 is 0.8 to 4.0 mm. Annular protrusions like those shown in the diagram are preferable as the protrusions 43 and 45. However, any configuration could be used as long as the protrusions restrict the movement of the stent 3 and can push it out. For example, they may be defined by a single protrusion or a plurality of protrusions provided integrally with the inner tube 4 or by a different member. Furthermore, the protrusions 43 and 45 may be formed by a different member composed of a radiopaque material. This allows the stent position to be accurately ascertained under radioscopy, which makes the procedure easier. The radiopaque material is preferably gold, platinum, platinum-iridium alloy, silver, stainless steel, platinum, or an alloy of the same. Furthermore, the protrusion is attached by forming a wire from a radiopaque material and winding it on the outer surface of the inner tube, or by forming a pipe from a radiopaque material and caulking the inner tube there to such that it is on the outer surface of the inner tube or bonding it on the outer surface of the inner tube.

Furthermore, the tapered part 44 formed on the proximal side of the protrusion 43 and the tapered part 46 formed on the proximal side of the protrusion 45 are formed by fixing a tapered member, or by applying a curable resin in a tapered manner and curing it, or any other method.

As shown in FIG. 2, the inner tube 4 has a lumen 41 extending from the distal end to at least a position of the proximal side relative to the stent housing portion 22 of the sheath 2, and an inner tube side hole 42 communicating with the lumen 41 at a position of the proximal side relative to the stent housing portion 22. In the stent delivery system 1 of this embodiment, the lumen 41 is terminated at the forming part of the side hole 42. The lumen 41 is used to insert one end of a guidewire from the distal end of the stent delivery system 1 and pass it partially through the inner tube such that it can then be led out to an external position from the inner tube side surface. Furthermore, the inner tube side hole 42 is located slightly toward the distal side of the stent delivery system 1 relative to a sheath side hole 21. It is preferable that the center of the inner tube side hole 42 is closer to the distal side than the center of the sheath side hole 21 by 0.5 to 10 mm and, more particularly, closer to the distal side by 1 to 2 mm. Furthermore, by setting a longer length as the distance between the center of the inner tube side hole 42 and the center of the sheath side hole 21, the curvature of the guidewire located between the inner tube side hole 42 and the sheath side hole 21 becomes gentler, so that insertion of the guidewire and the operability of the stent delivery system become more favorable.

The stent delivery system is not limited to one of the above-described type and the above-described lumen 41 may be one extending to the proximal end of the inner tube. In this case, the sheath side hole 2 is unnecessary.

The outer diameter of the inner tube 4 is preferably 1.0 to 2.5 mm and, more particularly, 1.0 to 2.0 mm is preferable. Furthermore, the length of the inner tube 4 is preferably 400 to 2500 mm and, more particularly, 400 to 2200 mm is preferable. In addition, the inner diameter of the lumen 41 is preferably 0.5 to 2.0 mm and, more particularly 0.5 to 1.5 mm. Moreover, the length of the lumen 41 is preferably 10 to 400 mm and, more particularly, 50 to 350 mm is preferable. Furthermore, it is preferable that the position of the side hole 42 is located toward the proximal side relative to the distal end of the inner tube 4 by 10 to 400 mm, more particularly toward the proximal side by 50 to 350 mm. In addition, it is preferable that the position of the side hole 42 is located toward the proximal side relative to the proximal end of the disposed stent 3 (in other words, the proximal end of the stent housing portion) by 50 to 250 mm.

It is preferable that the forming material of the inner tube 4 is a material having hardness and flexibility. For example, polyolefin such as polyethylene and polypropylene, nylon, polyethylene terephthalate, fluorine-based polymer such as ETFE, PEEK (polyetheretherketone), polyimide, etc. can be favorably used. The outer surface of the inner tube 4 may be coated with a material being biocompatible, particularly antithrombotic. Examples of the antithrombotic material that can be favorably used include poly(hydroxyethyl methacrylate), a copolymer of hydroxyethyl methacrylate and styrene (e.g. HEMA-St-HEMA block copolymer).

Moreover, it is preferable that the outer surface of the part of the inner tube 4 that is possibly exposed from the sheath 2 has lubricity. For this purpose the following are examples of a hydrophilic polymer that may be applied as a coating or fixed thereto: poly(2-hydroxyethyl methacrylate), poly(hydroxyethyl acrylate), hydroxypropyl cellulose, methyl vinyl ether maleic anhydride copolymer, polyethylene glycol, polyacrylamide, polyvinylpyrrolidone, dimethylacrylamide-glycidyl methacrylate copolymer, etc. Furthermore, the above-described material may be applied as a coating or fixed to the entire outer surface of the inner tube 4. Moreover, the above-described material may be applied as a coating or fixed also to the inner surface of the inner tube 4 in order to enhance the capability of sliding on the guidewire.

Furthermore, the inner tube 4 penetrates the sheath 2 and protrudes beyond the proximal-end opening of the sheath 2. As shown in FIG. 1 and FIG. 6, the inner tube hub 7 is bonded to the proximal portion of the inner tube 4.

Moreover, in the stent delivery system 1 of this embodiment, a hard pipe 72 is fitted to the proximal portion of the inner tube 4. This hard pipe 72 extends from the proximal portion of the inner tube 4 toward the distal side by a predetermined distance, and at least the distal part of the pipe 72 enters the inside of the sheath hub 6 and extends to a position toward the distal end relative to the valve body 62. This prevents kinking of the inner tube 4 at the proximal end of the sheath hub 6 and counters compression of the valve body 62. As the hard pipe, a metal pipe or a hard resin pipe can be used, for example.

Furthermore, it is preferable that a movement restrictor be provided at the proximal portion of the inner tube 4 to restrict the distance of the movement of the sheath 2 toward the proximal side. In this embodiment, the inner tube 4 has a movement restriction tube 73 at the proximal portion. This tube 73 has an outer diameter larger than the inner diameter of the pathway of the operation member 64 of the sheath hub 6 and is incapable of entering the inside of the sheath hub 6. Thus, this tube restricts the distance of the movement of the sheath toward the inner tube proximal end. In this embodiment, the tube 73 is provided so as to enclose the above-described hard pipe 72. The movement restrictor is not limited to the above-described tube body and may be formed by fixing an annular member to the side surface of the proximal portion of the inner tube 4.

Furthermore, the material explained for the sheath hub 6 can be favorably used as the forming material of the inner tube hub 7.

Figure 7:
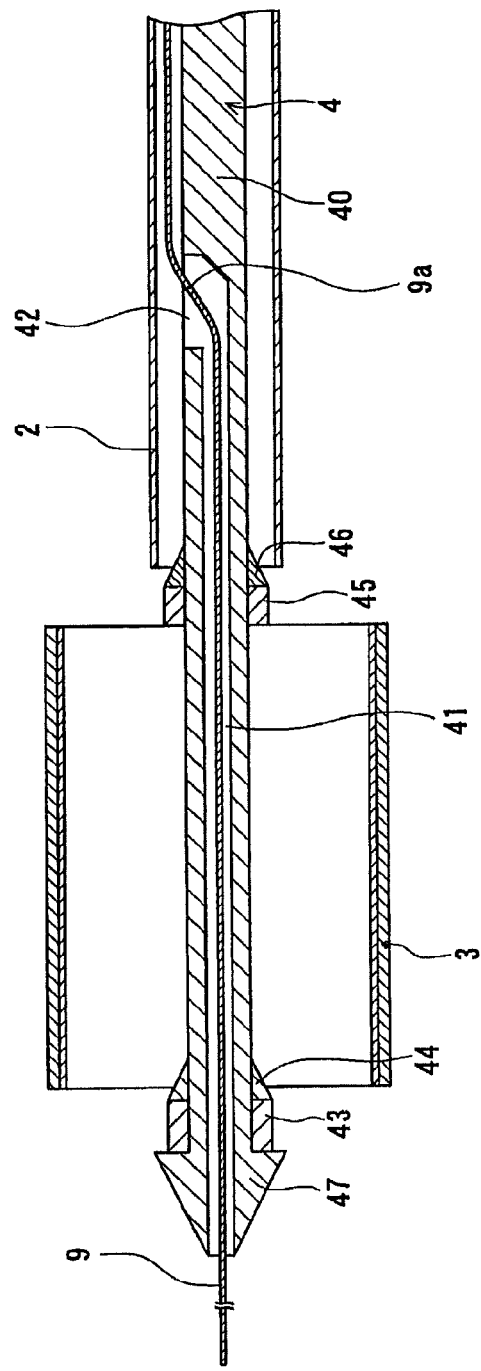
FIG. 7 is an explanatory diagram for explaining the operation of the stent delivery system disclosed here.

The stent 3 of the example of the present invention is a self-expandable stent. As shown in FIG. 3, in the sheath, the stent 3 is held in such a state as to press the inner surface of the sheath 2 by its own restoring force. Due to discharge of the stent 3 from the distal-end opening of the sheath 2, the applied stress is released and the stent 3 is expanded and restored to the shape before the compression as shown in FIG. 7. Furthermore, the stent 3 is disposed between the protrusions 43 and 45 provided on the inner tube 4 in the sheath 2 and the movement thereof in the sheath 2 is restricted. The stent may have any shape as long as it is a so-called self-expandable stent.

The stent 3 is formed into a substantially cylindrical shape. It is compressed in the center axis direction when being inserted into a living body and is capable of being expanded outward to be restored to the shape before the compression when being indwelled in the living body.

Figure 8:
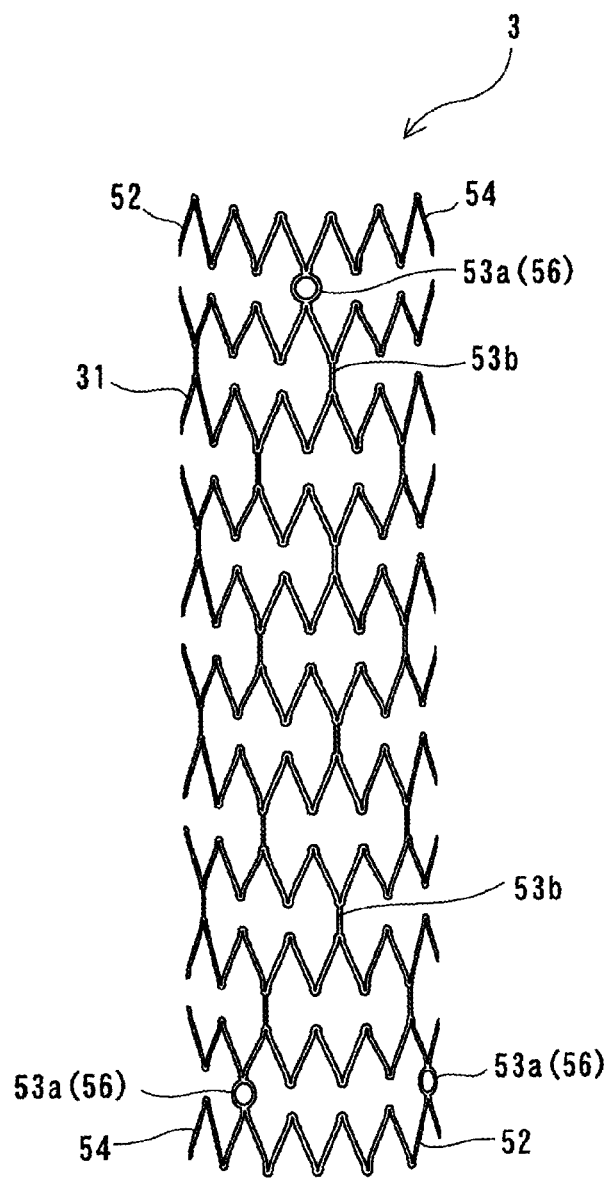
FIG. 8 is a perspective view of one example of a self-expandable stent used in the stent delivery system disclosed here.
Figure 9:
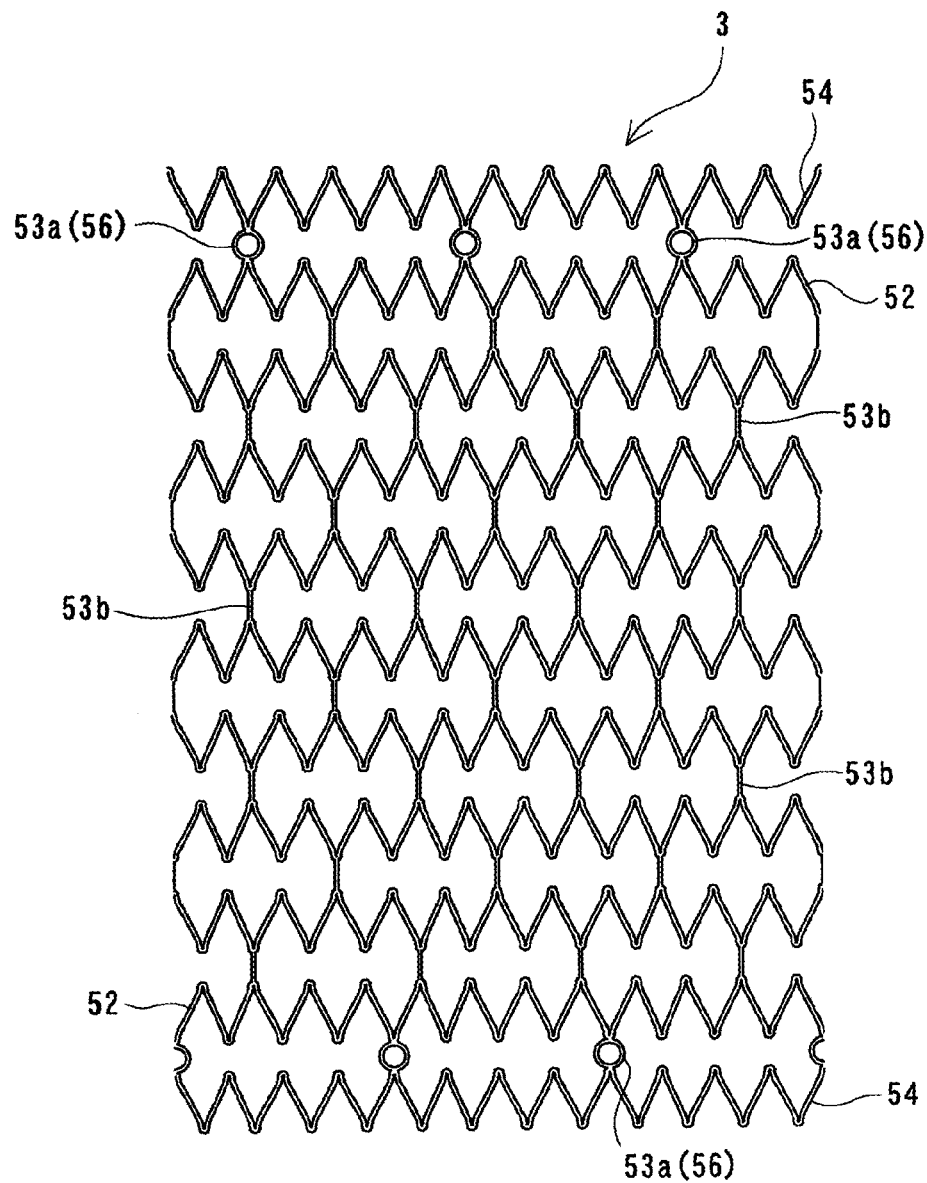
FIG. 9 is a development view of the self-expandable stent shown in FIG. 8.

As shown in FIG. 8 and FIG. 9, the stent 3 used in this example has an opening portion on the side surface. Furthermore, the stent 3 is configured by plural annular bodies 52 composed of linear bodies 54 that assume a role of maintaining expansion and are linked in a wave manner (zigzag manner) and an annular manner. The annular bodies 52 adjacent to each other in the axial direction are connected by a connecting portion 53 (connector) so as not to be separated from each other. The portion other than the portion configuring the annular bodies 52 and the connecting portions 53 forms the opening portion.

Furthermore, in the stent 3 of this example, the plural annular bodies 52 are arranged substantially linearly in such a manner that the valleys and peaks of the wave-like annular bodies 52 that are adjacent to each other in the axial direction also face each other. In this example, eleven annular bodies 52 are linked in the axial direction. Furthermore, one annular body 52 is formed by twelve peaks (valleys). Although the number of peaks (valleys) configuring one annular body 52 is selected accordingly depending on the diameter and length of the stent, it is preferable that the number is 4 to 36. It is preferable that 5 to 50 annular bodies 52 are linked in the axial direction.

The connecting portion 53 includes a connecting portion 53*a* having a circular shape at the portions closest to one end and the other end of the stent 3. In the other portion, other than the end portions, the connecting portion 53 is a linear connecting portion 53*b*. Partially connecting the adjacent annular bodies 52 to each other in this manner allows the stent 3 to easily curve along a body cavity. The circular connecting portion 53*a* is the portion to which a radiopaque marker 56 may be attached, as described below.

The circular connecting portion 53*a* links the annular bodies 52 to each other in such a manner that the peak and valley of the adjacent annular bodies 52 adjoin in the axial direction. The adjacent peak and valley are linked to the upper end and lower end, respectively, of the circular connecting portion 53*a*. The linear connecting portion 53*b* links the annular bodies 52 to each other in such a manner that the peak and valley of the adjacent annular bodies 52 adjoin in the axial direction. The linear connecting portion 53*b* may be in either a straight line manner or a curved line manner.

It is preferable that the circular connecting portion 53*a* and the linear connecting portion 53*b* are disposed at such positions so as to be at substantially equal angles with respect to the center axis. The circular connecting portion 53*a* is preferably formed at three places between the adjacent annular bodies, in other words, at every fourth peak (valley) (every 120°). Furthermore, the linear connecting portion 53*b* is preferably formed at four places between the adjacent annular bodies, in other words, at every third peak (valley) (every 90°). In the example of the embodiment disclosed here, the linear connecting portions 53*b* closest to each other in the axial direction are disposed so as to be shifted from each other by one and half peaks (valleys). Alternatively to the illustrated embodiment, all connecting portions may be linear connecting portions.

Furthermore, although different depending on the indwelled target portion, generally the outer diameter of the stent 3 is 2.0 to 30 mm, preferably 2.5 to 15 mm. The wall thickness is 0.04 to 1.0 mm, preferably 0.06 to 0.5 mm. The length is 5 to 150 mm, preferably 20 to 60 mm. In particular, in the case of a stent for indwelling in a blood vessel, the outer diameter is 2.0 to 14 mm, preferably 2.5 to 10 mm. The wall thickness is 0.04 to 0.3 mm, preferably 0.06 to 0.2 mm. The length is 5 to 80 mm, preferably 10 to 60 mm.

As described above, in the stent 3 of this example, the annular body 52 is composed of the linear bodies 54 linked in a wave manner (zigzag manner) and an annular manner as described above. It is preferable that the number of waves is about 4 to 36 and particularly 8 to 24. The length of the annular body 52 is 1 to 10 mm, preferably 1.5 to 5 mm. Furthermore, the number of annular bodies 52 is 5 to 50, preferably 5 to 20. In addition, it is preferable that the distance between the annular bodies 52 is 0.2 to 10 mm. Moreover, it is preferable that the length of the connecting portion 53 is 0.2 to 10 mm. Furthermore, it is preferable that the width of the linear body configuring the connecting portion is small so that the linear body can be bent by small force. Specifically, the width of the linear body 54 configuring the connecting portion 53 is 0.03 to 0.2 mm, preferably 0.05 to 0.12 mm.

The shape of the stent 3 is not limited to the above-described shape as long as it is such a shape that diameter reduction is possible in insertion in a living body and diameter enlargement (restoration) is possible in discharge in the living body. For example, the stent 3 may be one having a coil shape, cylindrical shape, roll shape, irregular tube shape, supercoil shape, leaf spring coil shape, or basket or mesh shape.

It is preferable that the stent 3 is integrally formed without the formation of a sudden change point of the properties as a whole. The stent 3 is preferably fabricated by preparing a metal pipe having an outer diameter compatible with the part in a living body where the stent 3 is to be indwelled and partially removing the side surface of the metal pipe by cutting processing, chemical etching, or the like.

A superelastic metal is preferable as the material to form the stent 3. A superelastic alloy is favorably used as the superelastic metal. The term "superelastic alloy" here is generally called the shape-memory alloy and shows superelasticity at least at a living body temperature (near 37° C.). The following superelastic alloys are favorably used: Ti—Ni alloy containing 49 to 53 atomic % of Ni, Cu—Zn alloy containing 38.5 to 41.5 weight % of Zn, Cu—Zn—X alloy containing 1 to 10 weight % of X (X=Be, Si, Sn, Al, Ga), Ni—Al alloy containing 36 to 38 atomic % of Al, etc. The above-described Ti—Ni alloy is particularly preferable. Furthermore, the mechanical properties can be changed accordingly by employing a Ti—Ni—X alloy (X=Co, Fe, Mn, Cr, V, Al, Nb, W, B, etc.) obtained by replacing part of the Ti—Ni alloy by 0.01 to 10.0% of X or employing a Ti—Ni—X alloy (X=Cu, Pb, Zr) obtained by replacing part of the Ti—Ni alloy by 0.01 to 30.0% of the atom and selecting the condition of the cold working ratio or/and final heat treatment. In addition, the mechanical properties can be changed accordingly by using the above-described Ti—Ni—X alloy and selecting the condition of the cold working ratio and/or final heat treatment.

The buckling strength (yield stress under load) of the superelastic alloy used is about 5 to 200 kg/mm$^2$ (22° C.), preferably 8 to 150 kg/mm$^2$. The restorative stress (yield stress during unloading) is about 3 to 180 kg/mm$^2$ (22° C.), preferably 5 to 130 kg/mm$^2$. The term "superelasticity" here means that, even when the alloy is deformed (bent, stretched, compressed) to a region where a normal metal is plastically deformed at a use temperature, the alloy is substantially restored to the shape before the compression without requiring heating after release of the deformation.

It is preferable for the stent 3 to have the radiopaque material marker 56. In particular, it is preferable for the radiopaque material marker to have a predetermined surface area. It is preferable for the radiopaque material marker 56 to be provided on the end portion of the stent. In the illustrated example, the radiopaque material marker 56 is provided at the plural circular connecting portions 53*a* located at both end portions of the stent 3. The radiopaque material marker 56 is fixed to the stent in such a manner as to occlude the small opening formed at the connecting portion 53*a*. It is preferable that such a marker is attached by disposing, in a small opening formed in the stent, a disc-like member of a radiopaque material slightly smaller than this small opening and pressing it from both surfaces to perform caulking. The radiopaque material marker may be any object and is not limited to the above-described object. For example, the marker may be obtained by covering the outer surface of the stent by a radiopaque material. Furthermore, the marker may be an object around which a wire formed from a radiopaque material is wound, and an object to which a ring-like member formed from a radiopaque material is attached. As the forming material of the radiopaque material marker, gold, platinum, gold, tungsten, tantalum, alloy of them, or silver-palladium alloy is preferable.

Furthermore, the stent delivery system 1 of the present invention is particularly effective when the stent having the above-described radiopaque material marker is used. As described above, the inner surface of the sheath 2, in which the stent 3 is housed, is a substantially polygonal prism inner surface. Therefore, the contact area between the inner surface of the sheath 2 and the surface of the radiopaque material marker 56 also decreases. Thus, sliding resistance attributed to the marker in discharge of the stent 3 can be decreased.

Next, a method for using the stent delivery system 1 of the present invention will be described with use of diagrams.

First, as shown in FIG. 2 and FIG. 7, a proximal portion 9a of a guidewire 9 is inserted from the distal end of the lumen 41 of the inner tube 4 and is made to pass through the side hole 42 of the inner tube 4 and the side hole 21 of the sheath 2 to be led out to an external region. Thereafter, with the sheath 2 grasped, the stent delivery system 1 of the present invention is inserted into a body cavity (e.g. blood vessel) along the guidewire 9 and the stent 3 is disposed in the target stenosis.

Next, the sheath 2 is moved toward the proximal side in the axial direction. At this time, the proximal-end surface of the stent 3 abuts on the distal-end surface of the stent pushing-out protrusion 45 and the stent 3 is locked. Thus, the stent 3 is discharged from the distal-end opening of the sheath 2 in association with the movement of the sheath 2. Due to this discharge, as shown in FIG. 7, the stent 3 is self-expanded to expand the stenosis and is indwelled in the stenosis. Thereafter, the inner tube 4 is moved toward the proximal side in the axial direction and is housed in the sheath 2, and the sheath 2 is removed from the inside of the body cavity together with the inner tube 4. Thereby, the procedure is ended. In the stent delivery system 1 of the embodiment disclosed here, the tapered part 44, in which the diameter is gradually reduced toward the proximal side, is formed near the proximal side of the protrusion 43 of the inner tube 4. Therefore, the sheath 2 does not get stuck on the protrusion 43 when the inner tube 4 is housed in the sheath 2.

Next, a stent delivery system according to another embodiment will be described with reference to FIGS. 10-20.

A stent delivery system 100 of this embodiment includes a stent 103 formed into a substantially cylindrical shape, an inner tube body having a guidewire lumen, and a stent housing tube body 105 that houses the stent 103 in the distal portion. The stent 103 is compressed in the center axis direction when being inserted into a living body and is capable of being expanded outward to be restored to its original shape before the compression when being indwelled in the living body. Furthermore, the stent 103 is disposed so as to cover the distal portion of the inner tube body, and the stent 103 can be exposed (can be discharged) by moving the stent housing tube body 105 toward the proximal side relative to the inner tube body. Moreover, the inner surface of at least the housing portion of the stent 103, of the stent housing tube body 105, is a substantially polygonal prism inner surface extending along the axial direction of the stent housing tube body 105.

Furthermore, in the stent delivery system 100 of this embodiment, the inner tube body includes a distal-side tube 102 having the guidewire lumen, a proximal-side tube 104, and a fixing tube 108 having an opening 123 communicating with a guidewire lumen 121. The proximal portion of the distal-side tube 102 and the distal portion of the proximal-side tube 104 are fixed to the fixing tube 108. In addition, the stent housing tube body 105 encloses the distal side of the distal-side tube 102 and can slide in the proximal direction of the distal-side tube 102. Furthermore, the stent delivery system 100 has at least one pulling wire 106 that has one end fixed to the stent housing tube body 105 and extends in the proximal-side tube 104. The pulling wire 106 is used to move the stent housing tube body 105 toward the proximal side by pulling toward the proximal side of the proximal-side tube 104.

Further still, the stent delivery system 100 of this embodiment includes the distal-side tube 102 having the guidewire lumen 121, the proximal-side tube 104, and the fixing tube 108 having the opening 123 communicating with the guidewire lumen 121. The proximal portion of the distal-side tube 102 and the distal portion of the proximal-side tube 104 are fixed to the fixing tube 108. The stent delivery system 100 further includes the stent housing tube body 105 that encloses the distal side of the distal-side tube 102 and can slide in the proximal direction of the distal-side tube 102, and the stent 103 housed in the stent housing tube body 105. The stent delivery system 100 further includes the pulling wire 106 (106a, 106b) that has one end fixed to the stent housing tube body 105 and extends in the proximal-side tube 104. The pulling wire 106 defines a movement means for moving the stent housing tube body 105 toward the proximal side by pulling toward the proximal side of the proximal-side tube.

Furthermore, the distal-side tube 102 has a stent proximal part locking portion 122 located on the distal side. The stent proximal part locking portion 122 abuts on the proximal end of the stent 103 housed in the stent housing tube body 105 and restricts the movement of the stent 103 toward the proximal side.

The stent 103 is formed into a substantially cylindrical shape and is housed in the stent housing tube body 105 in a state such that it is compressed in the center axis direction. When being discharged from the stent housing tube body 105, the stent 103 is expanded outward to be restored to the shape before the compression.

Furthermore, the stent delivery system 100 includes a slide tube 107 that is disposed so as to be close to the proximal end of the stent housing tube body 105. The fixing tube 108 can house the slide tube 107 from the proximal side. The slide tube 107 can move toward the proximal side together with the stent housing tube body 105 by pulling on the pulling wire 106 and is not fixed to the stent housing tube body 105. Moreover, the slide tube 107 includes a slide tube main body 171 and a distal-side tubular member 172 that is fixed to the distal portion of the slide tube main body 171 and covers the distal end of the slide tube main body 171. The distal-side tubular member 172 extends beyond the distal end of the slide tube main body 171 toward the distal side of the stent delivery system 100. In addition, the distal-side tubular member 172 is an integrally-shaped tubular body having a reduced diameter part 173 that is located between the distal end and proximal end of the distal-side tubular member 172 and has a reduced inner diameter.

Furthermore, in the stent delivery system 100 of this embodiment, the outer diameter of the proximal-side tube 104 is smaller than the outer diameter of the largest diameter part in the area toward the distal end relative to the proximal-side tube 104 of the stent delivery system 100. Therefore, even in the state in which a guidewire extending from the opening 123 toward the proximal side is disposed along the side surface of the proximal-side tube, the total outer diameter can be set equivalent to the outer diameter of the largest diameter part in the area toward the distal side relative to the proximal-side tube of the stent delivery system, and insertion into a blood vessel with a small diameter is possible.

Furthermore, the stent delivery system 100 of this embodiment has a pulling wire winding-up mechanism for winding up the pulling wire 106 to move the stent housing tube body 105 toward the proximal side at the proximal portion of the proximal-side tube 104.

The stent delivery system 100 thus includes the distal-side tube 102, the stent 103, the proximal-side tube 104, the stent housing tube body 105, the pulling wire 106, the slide tube 107, the fixing tube 108, and an operation section 110 having the winding-up mechanism of the pulling wire 106. Furthermore, the fixing tube 108 connects the distal-side tube 102 and the proximal-side tube 104 and has the opening 123 communicating with the proximal portion of the distal-side tube 102.

Figure 10:
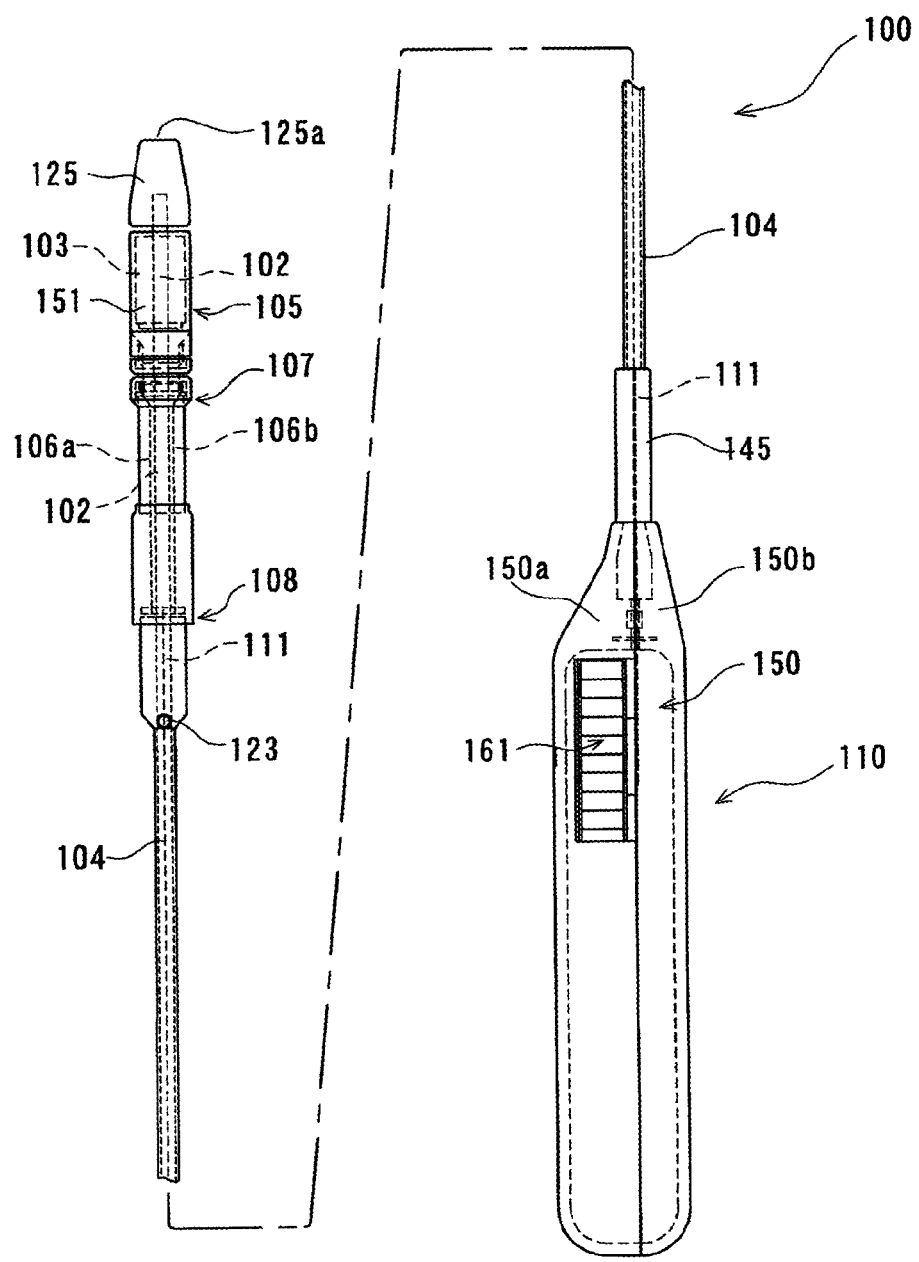
FIG. 10 is a partially omitted external view of a stent delivery system according to another embodiment disclosed here by way of example.
Figure 11:
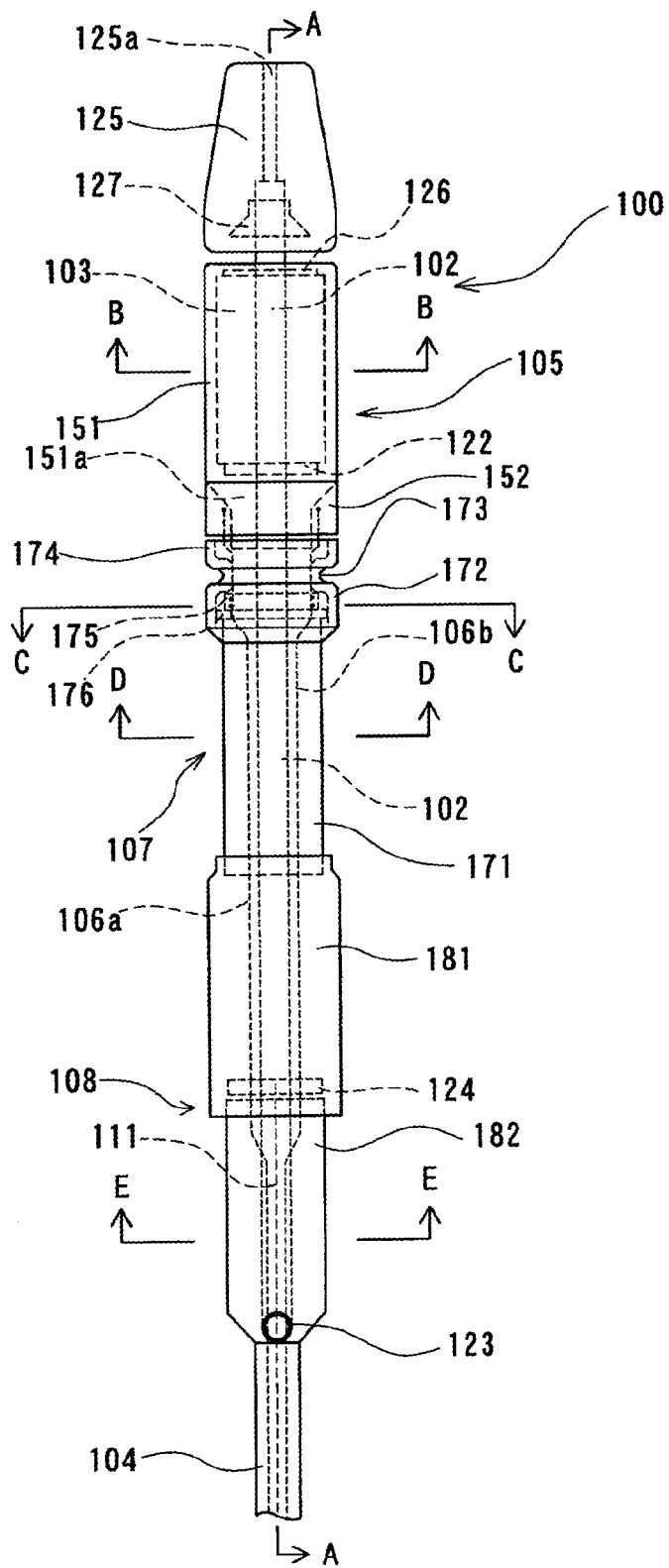
FIG. 11 is an enlarged external view of the distal portion of the stent delivery system of FIG. 10.
Figure 12:
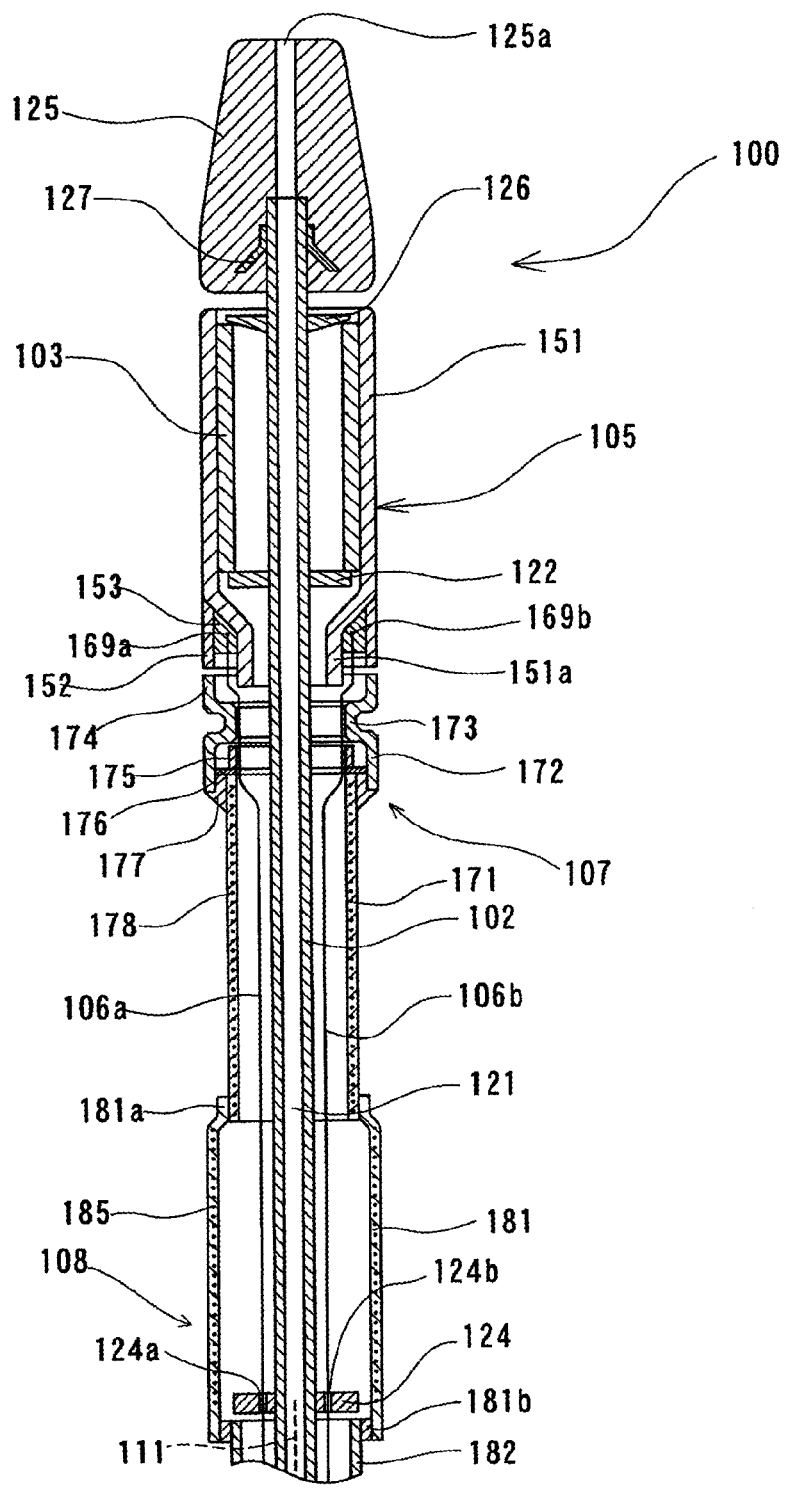
FIG. 12 is an enlarged sectional view of the distal portion of the stent delivery system of FIG. 10.
Figure 13:
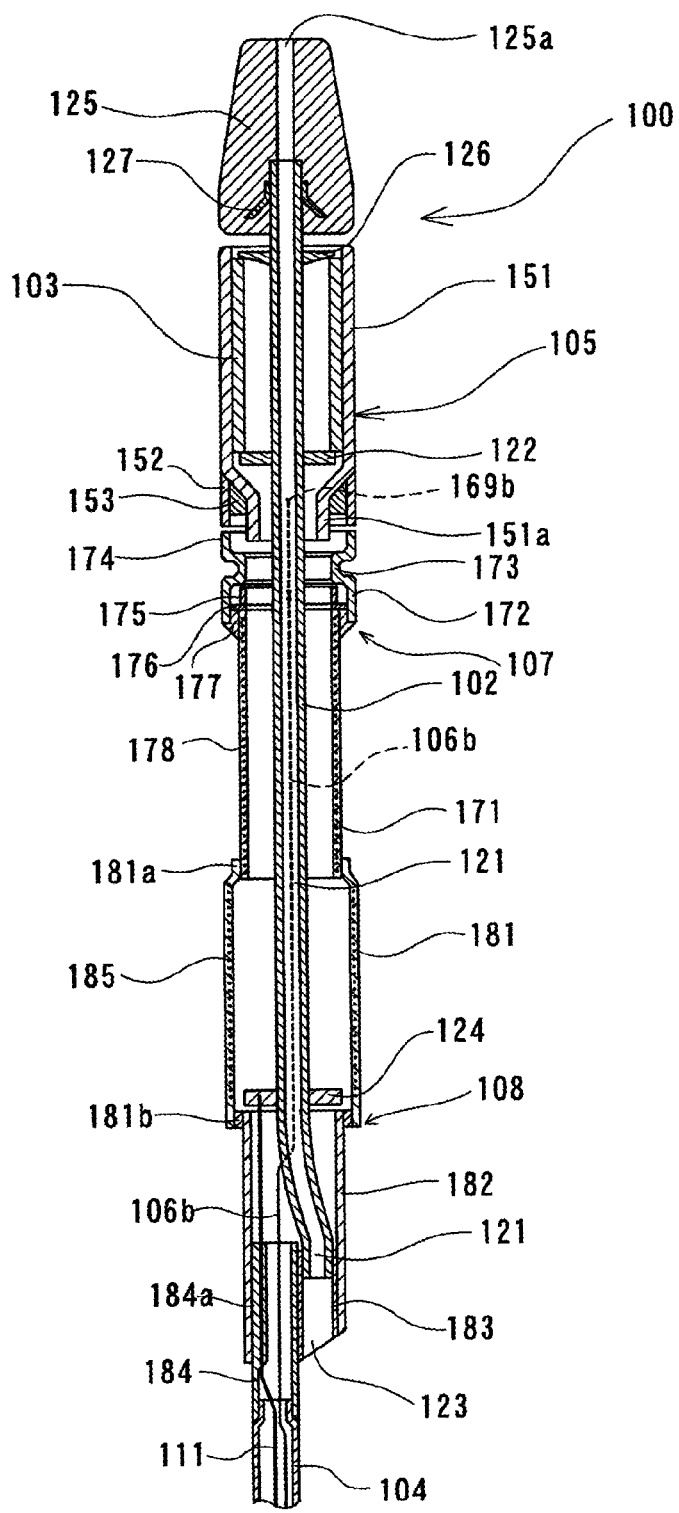
FIG. 13 is a sectional view along line XIII-XIII in FIG. 11.

As shown in FIGS. 10-20, the distal-side tube 102 is a tube body having the guidewire lumen 121 penetrating from the distal end to the proximal end. The distal portion thereof is formed by a distal-end member 125 fixed to the distal end and the distal end thereof has a distal-end opening 125a. The distal portion may be formed integrally with the distal-side tube. Furthermore, the distal-side tube 102 is fixed to the fixing tube 108 at the proximal portion. In addition, the proximal end of the distal-side tube 102 communicates with the opening 123 formed in the fixing tube 108. Moreover, the proximal portion of the distal-side tube 102 is curved as shown for example in FIG. 13. Furthermore, the opening 123 is obliquely formed in such a manner as to incline toward the proximal side as shown in FIG. 10 and FIG. 13. This makes induction of the guidewire easy.

The distal-side tube 102 is a tube body having the guidewire lumen 121 penetrating from the distal end to the proximal end as shown in the figures. The distal-side tube 102 preferably has an outer diameter of 0.3 to 2.0 mm, preferably 0.5 to 1.5 mm. The inner diameter is 0.2 to 1.5 mm, preferably 0.3 to 1.2 mm. The length is 20 to 600 mm, preferably 30 to 450 mm.

Furthermore, it is preferable for the distal-end member 125 to be located toward the distal side relative to the distal end of the stent housing tube body 105 and, as shown in FIG. 10 and FIG. 13, be formed into a tapered shape in which the diameter is gradually reduced toward the distal end. Forming the distal-end member 125 in this manner facilitates insertion into a stenosis. In addition, it is preferable for the distal-side tube 102 to have a stopper provided toward the distal side relative to the stent 3 in order to restrict the movement of the stent housing tube body in the distal direction. In this embodiment, the proximal end of the distal-end member 125 can abut on the distal end of the stent housing tube body 105 and function as the above-described stopper.

It is preferable that the outer diameter of the most distal part of the distal-end member (distal part) 125 is 0.5 to 1.8 mm. Furthermore, it is preferable that the outer diameter of the largest diameter part of the distal-end member (distal part) 125 is 0.8 to 4.0 mm. Moreover, it is preferable that the length of the tapered part is 2.0 to 20.0 mm.

Furthermore, as shown in FIG. 12 and FIG. 13, the distal-side tube 102 has the stent proximal part locking portion 122 provided at a position toward the proximal side relative to the distal end of the tube 102 by a predetermined distance in order to restrict the movement of the stent 103 toward the proximal side. It is preferable for the locking portion 122 to be an annular protrusion. In addition, the area toward the distal side relative to this stent proximal part locking portion 122 is the stent housing portion. The outer diameter of this locking portion 122 is configured such that it can abut on the proximal end of the compressed stent 103. Furthermore, even when the stent housing tube body 105 moves toward the proximal side, the stent 103 is kept in the position due to the locking portion 122 and thus is discharged from the stent housing tube body 105 as a result.

Furthermore, in the stent delivery system 100 of this embodiment, as shown in FIG. 12 and FIG. 13, the distal-side tube 102 has a stent distal part locking portion 126 provided at a position toward the distal side relative to the stent proximal part locking portion 122 by a predetermined length (substantially the stent length in the axial direction). As shown in FIG. 12 and FIG. 13, the stent distal part locking portion 126 is located slightly toward the proximal side relative to the distal end of the stent housing tube body 105. It is preferable for the locking portion 126 to be an annular protrusion. Furthermore, the portion between this stent distal part locking portion 126 and the stent proximal part locking portion 122 is the stent housing portion. The outer diameter of this locking portion 126 is configured such that it can abut on the distal end of the compressed stent 103. Moreover, the proximal-end surface of the stent distal part locking portion 126 is a tapered surface in which the diameter is reduced in the proximal direction. Thus, in stent discharge, the stent distal part locking portion 126 does not become an obstacle. Furthermore, withdrawal of the stent delivery system 100 (specifically, the housing in a guiding catheter or the sheath) after the discharge of the stent 103 is easy.

It is preferable that the outer diameter of the stent proximal part locking portion 122 and the stent distal part locking portion 126 is 0.8 to 4.0 mm. Annular protrusions like those shown in the figures are preferable as the stent proximal part locking portion 122 and the stent distal part locking portion 126. However, any configuration is acceptable if the protrusions can restrict the movement of the stent 103 and can push it out. For example, they may comprise one or a plurality of protrusions provided integrally with the distal-side tube 102 or with a different member. Furthermore, the stent proximal part locking portion 122 and the stent distal part locking portion 126 may be formed by a different member composed of a radiopaque material. This allows the stent position to be accurately grasped under radiopacity, which makes the procedure easier. The radiopaque material is preferably gold, platinum, platinum-iridium alloy, silver, stainless steel, platinum, or an alloy thereof. Furthermore, the protrusion is attached by forming a wire from a radiopaque material and winding it on the outer surface of the distal-side tube, or by forming a pipe from a radiopaque material and caulking the inner tube thereto such that it is on the outer surface of the inner tube or bonding it to the outer surface of the inner tube.

It is preferable that the forming material of the distal-side tube is a material having hardness and flexibility. For example, the following resins can be favorably used: polyolefin such as polyethylene and polypropylene, polyamide, polyester such as polyethylene terephthalate, fluorine-based polymer such as ETFE, PEEK (polyetheretherketone), polyimide, etc. In particular, among the above-described resins, a resin having thermoplasticity is preferable. The outer surface to be exposed, of the distal-side tube, may be coated with a material being biocompatible, particularly antithrombotic. The antithrombotic material may be, for example, poly(hydroxyethyl methacrylate), a copolymer of hydroxyethyl methacrylate and styrene (e.g. HEMA-St-HEMA block copolymer), etc.

Furthermore, if the distal part is configured by a different member from the distal-side tube, it is preferable to use a material having flexibility as the distal part (distal-end member) 125. For example, the following synthetic resin elastomers may be used: olefin-based elastomer (e.g. polyethylene elastomer, polypropylene elastomer), polyamide elastomer, styrene-based elastomer (e.g. styrene-butadiene-styrene copolymer, styrene-isoprene-styrene copolymer, styrene-ethylenebutylene-styrene copolymer), urethane-based elastomer, and fluorine resin-based elastomer. In addition, the following rubber materials may be used: synthetic rubber such as urethane rubber, silicone rubber, and butadiene rubber; and natural rubber such as latex rubber.

In particular, in the stent delivery system 100 of this embodiment, the distal-side tube 102 and the distal-end member 125 are formed by different members and a stopper member 127 is fixed at the distal portion of the distal-side tube 102. The stopper member 127 includes a tubular part fixed to the distal-side tube 102 and a skirt part spread from the tubular part in a tapered manner. Furthermore, the stopper member 127 is in such a state as to be embedded in the distal-end member 125 and prevents the distal-end member 125 from being separated and moving toward the distal side. It is preferable for the stopper member 127 to be formed by a metal (e.g., stainless steel).

As shown in FIG. 10, FIG. 11, and FIG. 13, the proximal-side tube 104 is a tube body penetrating from the distal end to the proximal end and includes the operation section 110 fixed to the proximal end. The distal portion of the proximal-side tube 104 is bonded to the fixing tube 108 by a fixing member 184. The proximal-side tube 104 defines, in an interior thereof, a pulling wire lumen in which the pulling wire 106 can be inserted.

The length of the proximal-side tube 104 is about 300 to 1500 mm, preferably 1000 to 1300 mm. The outer diameter is about 0.5 to 1.5 mm, preferably 0.6 to 1.3 mm. The inner diameter is about 0.3 to 1.4 mm, preferably 0.5 to 1.2 mm.

The distance of the shift between the center axis of the proximal-side tube 104 and the center axis of the distal-side tube 102 is preferably 0.1 to 2.0 mm and, more particularly, 0.5 to 1.5 mm is preferable.

It is preferable that the forming material of the proximal-side tube be a material having hardness and flexibility. For example, polyolefin such as polyethylene and polypropylene, nylon, polyethylene terephthalate, fluorine-based polymer such as ETFE, PEEK (polyetheretherketone), polyimide, etc. can be favorably used. The outer surface of the proximal-side tube may be coated with a material being biocompatible, particularly antithrombotic. Examples of an antithrombotic material that can be used include poly(hydroxyethyl methacrylate), a copolymer of hydroxyethyl methacrylate and styrene (e.g. HEMA-St-HEMA block copolymer), etc. Furthermore, it is preferable to use a material having comparatively high rigidity as the forming material of the proximal-side tube 104. For example, a metal such as Ni—Ti, brass, stainless steel, and aluminum can be used. Moreover, it is also possible to use a resin having comparatively high rigidity, such as polyimide, vinyl chloride, and polycarbonate.

Figure 20:
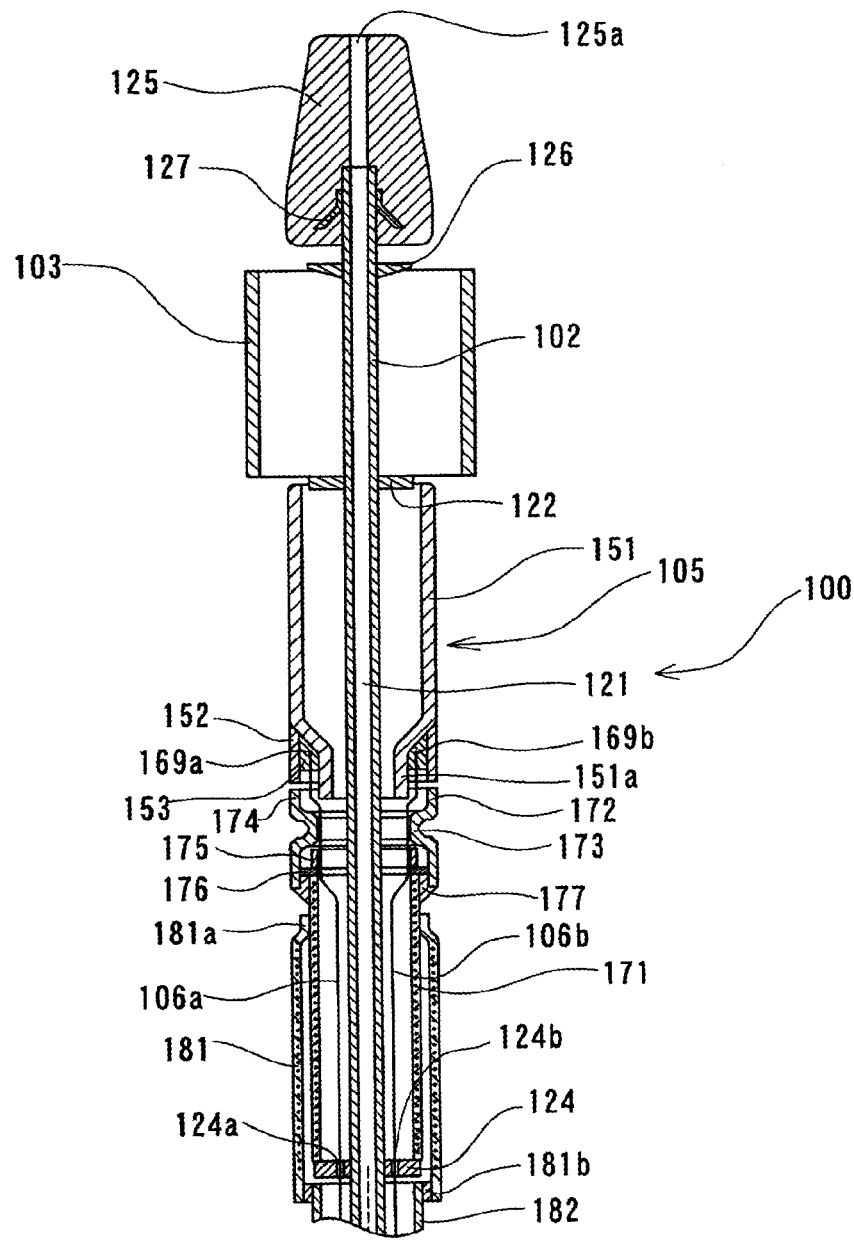
FIG. 20 is an explanatory diagram for explaining the operation of the stent delivery system of FIG. 10.

As shown in FIGS. 10-15 and FIG. 18, the stent housing tube body 105 is a tubular body having a predetermined length and the distal end and proximal end thereof are opened. The distal-end opening functions as a discharge port of the stent 103 when the stent 103 is indwelled at a stenosis in a body cavity. As shown in FIG. 20, the stent 103 is pushed out from this distal-end opening such that the stress load is released, and thus, the stent 103 is expanded and restored to the shape before the compression.

Figure 14:
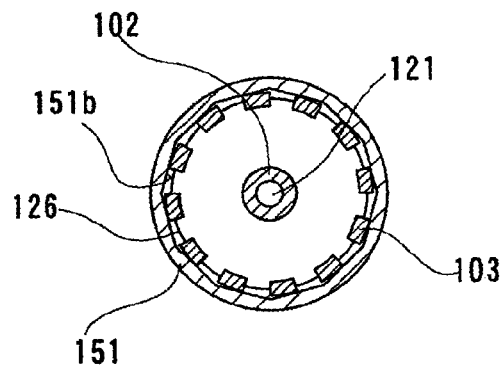
FIG. 14 is a sectional view along line XIV-XIV in FIG. 11.
Figure 15:
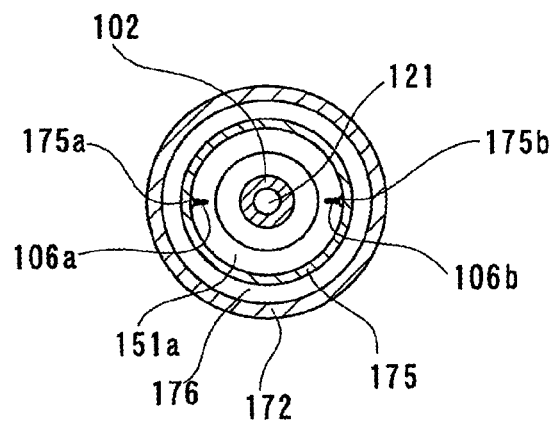
FIG. 15 is an enlarged view of a section along line XV-XV in FIG. 11.
Figure 16:
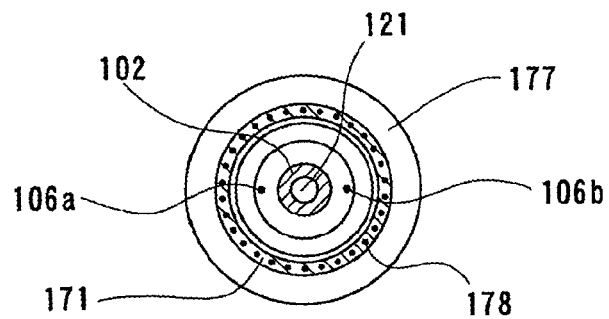
FIG. 16 is an enlarged view of a section along line XVI-XVI in FIG. 11.

Furthermore, as shown in FIG. 14, an inner surface 151b of the stent housing tube body 105 from the distal end of the stent housing tube body 105 to the proximal part of the stent housing portion is a substantially polygonal prism inner surface extending along the axial direction of the stent housing tube body 105.

The length of the stent housing tube body 105 is preferably 20 to 400 mm and, more particularly, 30 to 300 mm is preferable. Furthermore, the outer diameter is preferably 1.1 to 4.0 mm and, more particularly, 1.5 to 3.0 mm is preferable. In addition, the inner diameter of the stent housing tube body 105 is preferably 1.0 to 2.5 mm.

Furthermore, the stent housing tube body 105 includes a tube body main body portion 151 having a small diameter part 151a provided at the proximal portion thereof and a tubular portion 152 provided so as to surround the small diameter part 151a. The proximal part of the small diameter part 151a protrudes beyond the tubular portion 152. Specifically, a distal part 169 (169a, 169b) of the pulling wire 106 (106a, 106b) enters the void formed between the small diameter part 151a and the tubular portion 152 and is fixed to the stent housing tube body 105 by a fixing agent 153 with which the void is filled. The small diameter part 151a has a tapered part in which the outer diameter is reduced toward the proximal side and a short cylindrical part extending from this tapered part toward the proximal side. Furthermore, the tubular portion 152 is fixed to the proximal portion of the tube body main body portion 151 in such a manner as to enclose the reduced diameter part 151a of the tube body main body portion 151. Thus, the small diameter part 151a of the tube body main body portion 151 defines an annular protrusion that protrudes toward the inside of the stent housing tube body 105 and in the proximal direction. Furthermore, an annular void part is formed between the outer surface of this annular protrusion and the inner surface of the tubular portion 152. In addition, in this embodiment, the distal part 169 (169a, 169b) of the pulling wire 106 (106a, 106b) is fixed at the outer surface of the small diameter part 151a. Moreover, this void part is filled with the fixing agent (adhesive), which makes the tube body main body portion 151 and the proximal-side tubular portion 152 integral. Furthermore, by the fixing agent or the like with which the annular void part is filled, the distal part (fixture point) 169 (169a, 169b) of the pulling wire 106 (106a, 106b) to be described later is fixed to the stent housing tube body 105. It is preferable to use an adhesive of epoxy resin, ultraviolet-curable resin, cyanoacrylate-based resin, etc. as the fixing agent. However, thermal fusion bonding may be employed.

Furthermore, in this embodiment, in the tube body main body portion 151 of the stent housing tube body 105, as shown in FIG. 14, the inner surface 151b from the distal end to the proximal part of the stent housing portion is a substantially polygonal prism inner surface extending along the axial direction of the tube body main body portion 151. This substantially polygonal prism inner surface 151b may further extend toward the proximal side beyond the proximal end of the stent housing portion. It is preferable that the substantially polygonal prism inner surface 151b extends along the axial direction of the tube body main body portion 151 (stent housing tube body 105) and has no substantial bent part. In particular, similar to the above-described embodiment shown in FIG. 4, it is preferable for the substantially polygonal prism inner surface 151b to be a polygonal prism inner surface extending in parallel to the axial direction (center axis) of the tube body main body portion 151 (stent housing tube body 105). Therefore, each inner surface portion forming the polygonal prism inner surface extends in parallel to the axial direction (center axis) of the tube body main body portion 151 (stent housing tube body 105). Furthermore, similar to the above-described embodiment shown in FIG. 5, the substantially polygonal prism inner surface may extend in a helical manner (preferably, gentle helical manner) with respect to the axial direction (center axis) of the tube body main body portion 151 (stent housing tube body 105). In this case, each inner surface portion of the substantially polygonal prism inner surface 151b extends in a helical manner (preferably, gentle helical manner) with respect to the axial direction (center axis) of the tube body main body portion 151 (stent housing tube body 105), similar to the one shown in FIG. 5.

Moreover, in all of the above-described embodiments, each inner surface portion configuring the substantially polygonal prism inner surface 151b may be one whose center part bulges toward the inside of the tube body main body portion 151 (stent housing tube body 105) as shown in FIG. 27. This can further decrease the contact area with the outer surface of the stent 103. It is preferable that the bulge part of each inner surface portion have no bent part and the center part of each inner surface portion slightly bulge. Furthermore, it is preferable that this bulge part is formed across the total length of each inner surface portion. In addition, this bulge part is one extending in parallel to the axial direction (center axis) of the tube body main body portion 151 (stent housing tube body 105). The bulge part may be one that corresponds to the shape of each inner surface portion and extends in a helical manner (preferably, gentle helical manner) with respect to the axial direction (center axis) of the stent housing tube body.

Furthermore, in all of the above-described embodiments, it is preferable that the substantially polygonal prism inner surface have a regular or symmetrical polygon shape. However, it may have a polygon in which the respective sides (circumferential widths of the respective inner surface portions) are not identical. In addition, the number of inner surface portions (the number of corners where the angled inner surface portions intersect) of the substantially polygonal prism inner surface is preferably 6 to 24 and, more particularly, 8 to 12 is preferable. Furthermore, the circumferential width of the respective inner surface portions of the substantially polygonal prism inner surface is preferably 0.1 to 1.3 mm and, more particularly, 0.3 to 1.0 mm is preferable.

Furthermore, in the stent housing tube body 105 used in this embodiment, the tube body main body portion 151 and the tubular portion 152 have substantially the same outer diameter. The outer diameter of the tube body main body portion 151 and the tubular portion 152 is preferably 1.0 to 4.0 mm and, more particularly, 1.5 to 3.0 mm is preferable. Furthermore, the length of the stent housing tube body 105 is preferably 20 to 400 mm and, more particularly, 30 to 300 mm is preferable. In addition, the length of the tube body main body portion 151 is preferably 10 to 200 mm and, more particularly, 15 to 150 mm is preferable. The length of the tubular portion 152 is preferably 10 to 200 mm and, more particularly, 15 to 150 mm is preferable.

The stent housing tube body 105 is not limited to the above-described embodiment composed of the tube body main body portion 151 and the tubular portion 152, and it may also be integrally formed instead.

The slide tube 107 is disposed so that its distal end is close to the proximal end of the stent housing tube body 105. Furthermore, the slide tube 107 can be housed in the fixing tube from its proximal side. The slide tube 107 may enclose the fixing tube 108 from its proximal side. The slide tube 107 can move toward the proximal side together with the stent housing tube body 105 by pulling the pulling wire 106 and it is not fixed to the stent housing tube body 105.

Furthermore, in the stent delivery system 100 of the disclosed embodiment, as shown in FIGS. 11-18, the slide tube 107 includes the slide tube main body 171 and the distal-side tubular member 172 that is fixed to the distal portion of the slide tube main body 171 by an adhesive 177 and covers the distal end of the slide tube main body 171. The distal-side tubular member 172 extends beyond the distal end of the slide tube main body 171 toward the distal side of the stent delivery system 100. In addition, the distal-side tubular member 172 is an integrally-shaped tubular body including the reduced diameter part 173 that is located between a distal part 174 and a proximal part of the distal-side tubular member 172 and has a reduced inner diameter. Furthermore, in this embodiment, the inner diameter of the reduced diameter part 173 is substantially equal to, or slightly larger than, or slightly smaller than the inner diameter of the slide tube main body 171. Moreover, in the stent delivery system 100 of this embodiment, as shown in FIGS. 11-18, the outer diameter and inner diameter of at least the part other than the reduced diameter part 173, of the distal-side tubular member 172, are larger than those of the slide tube main body 171.

Furthermore, in the stent delivery system 100 of this embodiment, a ring member 175 is housed between the distal end of the slide tube main body 171 and the reduced diameter part 173 of the distal-side tubular member 172. In addition, the pulling wires 106a and 106b are fixed to the ring member 175. Moreover, the inner diameter of the reduced diameter part 173 of the distal-side tubular member 172 is larger than the outer diameter of the distal-side tube 102. Thus, the distal-side tubular member 172 can move toward the proximal side without making contact with the distal-side tube 102. Furthermore, the inner diameter of the reduced diameter part 173 of the distal-side tubular member 172 is smaller than the outer diameter of the ring member 175. Thus, the movement of the ring member 175 in the distal direction is restricted. In addition, the slide tube 107 moves toward the proximal side together with the ring member 175 by pulling the pulling wires 106a and 106b toward the proximal side. Furthermore, the ring member 175 is fixed to neither the slide tube main body 171 nor the distal-side tubular member 172 and is rotatably housed between the distal end of the slide tube main body 171 and the reduced diameter part 173 of the distal-side tubular member 172. The distal-side tubular member 172 of the slide tube 107 permits rotation of the ring member 175, and large movement of the ring member 175 in the axial direction is substantially restricted by the reduced diameter part 173 and the distal end of the slide tube main body 171.

Because the ring member 175 is rotatable relative to the slide tube 107 in this manner, it is difficult for the ring member 175, the fixed part of the pulling wire, and also the pulling wire itself to follow rotation of the distal-side tubular member 172 (slide tube 107). Furthermore, a resin ring 176 may be disposed between the ring member 175 and the distal end of the slide tube main body 171. Disposing such a resin ring makes rotation of the ring member 175 easier. A resin ring having low frictional resistance is preferable. A fluorine-based polymer such as ETFE, PEEK (polyetheretherketone), polyimide, etc. can be favorably used for the resin ring.

Figure 18:
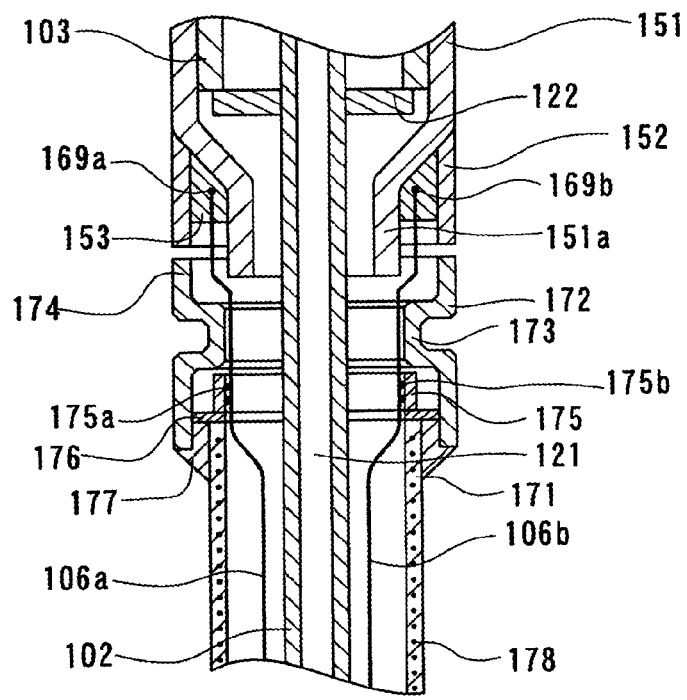
FIG. 18 is an enlarged sectional view in the vicinity of the proximal portion of a stent housing tube body and the distal portion of a slide tube in the stent delivery system of FIG. 10.

Furthermore, it is preferable that the distal part 174 of the distal-side tubular member 172 of the slide tube 107 encloses the proximal part of the small diameter part 151a of the stent housing tube body 105. In addition, it is preferable that the distal-side tubular member 172 of the slide tube 107 is not in contact with the stent housing tube body 105. In this embodiment, as shown in FIG. 13 and FIG. 18, the distal part of the distal-side tubular member 172 of the slide tube 107 encloses the proximal part of the small diameter part 151a of the stent housing tube body 105 without being bonded to and substantially making contact with the proximal part.

Moreover, in this embodiment, a reinforcing layer 178 is provided across the entirety of the slide tube main body 171. By providing such a reinforcing layer, the kink resistance is enhanced and the slide of the slide tube 107 becomes favorable. It is preferable for the reinforcing layer to be a mesh-like reinforcing layer. It is preferable for the mesh-like reinforcing layer to be formed by a braid wire. For example, a wire braid can be formed by a metal wire of stainless steel, elastic metal, superelastic metal, shape-memory alloy, etc. and having a wire diameter of 0.01 to 0.2 mm, more preferably 0.03 to 0.1 mm. Alternatively, the braid wire may be formed by a synthetic fiber such as polyamide fiber, polyester fiber, and polypropylene fiber.

In the stent delivery system 100 of this embodiment, as shown in FIGS. 11-13, FIG. 17, and FIG. 19, the fixing tube 108 includes a distal-side fixing tube 181 having a large outer diameter and a proximal-side fixing tube 182 fixed to the proximal portion of this distal-side fixing tube 181. Furthermore, the distal-side fixing tube 181 has a distal-end reduced diameter portion 181a and the inner surface of the distal-end reduced diameter portion 181a is in contact with the outer surface of the proximal portion of the slide tube 107. In addition, the slide tube 107 is not fixed to the distal-side fixing tube 181 and slides toward the proximal side to thereby enter the inside of the distal-side fixing tube 181 and be housed.

Figure 19:
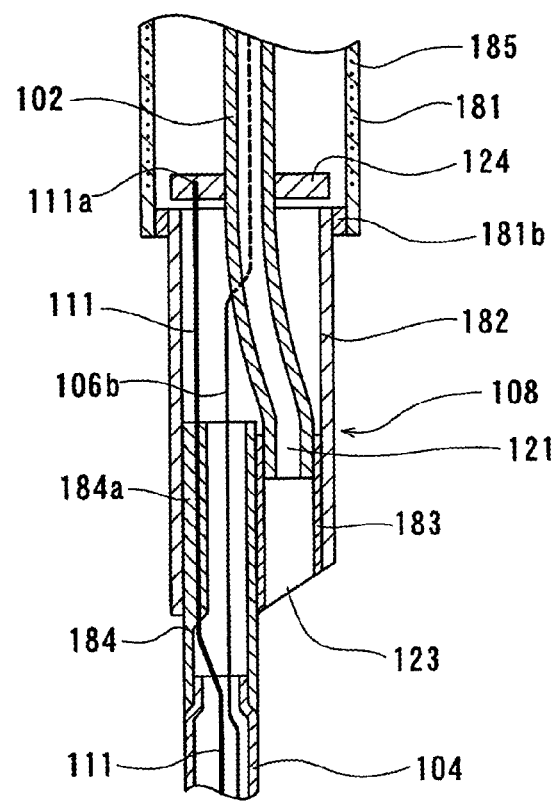
FIG. 19 is an enlarged sectional view in the vicinity of the proximal-side portion of a fixing tube of the stent delivery system of FIG. 10.

The distal portion of the proximal-side fixing tube 182 enters the inside of the proximal end of the distal-side fixing tube 181 and is fixed by a fixer 181b. Furthermore, a slide tube locking portion 124 is provided on the outer surface of the distal-side tube 102 in the fixing tube 108, specifically at a position at the proximal portion of the distal-side fixing tube 181 as shown in FIG. 19. The slide tube 107 can slide toward the proximal side until abutting on this slide tube locking portion 124. In other words, the slide tube 107 abuts on the slide tube locking portion 124 and further movement thereof toward the proximal side is thereby restricted.

Moreover, in this embodiment, as shown in FIG. 19, the distal-side portion of the fixing tube 108, specifically the distal-side fixing tube 181, has a reinforcing layer 185 across substantially the entirety thereof. The reinforcing layer is preferably formed as being mesh-like, helical, or the like. In particular, a mesh-like reinforcing layer is preferable. As the mesh-like reinforcing layer, one formed into a mesh manner by a metal thin wire is preferable. Stainless steel is preferable as the metal thin wire. Moreover, as shown in FIG. 19, it is preferable that the reinforcing layer 185 does not exist at the portion of the fixing tube 108 defining a connecting part which connects with the proximal-side fixing tube 182.

Figure 17:
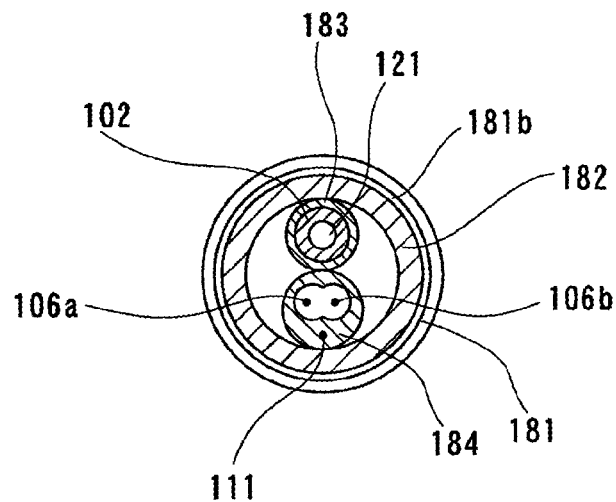
FIG. 17 is an enlarged view of a section along line XVII-XVII in FIG. 11.

The proximal portion of the distal-side tube 102 is provided with a tubular binding member 183 that houses this proximal portion. Furthermore, the distal end of the proximal-side tube 104 is provided with a tubular fixing member 184 that houses the distal portion thereof. In addition, as shown in FIG. 17 and FIG. 19, the tubular binding member 183 and the tubular fixing member 184 are bound to the proximal-side fixing tube 182.

Furthermore, as shown in FIG. 11 and FIG. 12, in this stent delivery system 100, the plural (specifically, two) pulling wires 106a and 106b are included and the fixture points 169a and 169b of the pulling wires 106a and 106b are fixed to the outside of the small diameter part 151a of the stent housing tube body 105 by the fixing agent 153 in the above-described void part defined by the stent housing tube body 105. In addition, the pulling wires 106a and 106b and these fixture points 169a and 169b are separated by a predetermined length.

The preferred forming material for the stent housing tube body 105 (tube body main body portion 151, tubular portion 152), the slide tube 107 (slide tube main body 171, distal-side tubular member 172), and the fixing tube 108 (distal-side fixing tube 181, proximal-side fixing tube 182) includes a polyolefin such as polyethylene and polypropylene, nylon, polyethylene terephthalate, polyimide, fluorine-based polymer such as PTFE and ETFE, and thermoplastic elastomers are preferable in view of the properties required for the stent housing tube body (flexibility, hardness, strength, slidability, kink resistance, stretch property). The thermoplastic elastomer may be an elastomer arbitrarily selected from nylon series (e.g., polyamide elastomer), urethane series (e.g. polyurethane elastomer), polyester series (e.g. polyethylene terephthalate elastomer), and olefin series (e.g., polyethylene elastomer, polypropylene elastomer).

Moreover, it is preferable to subject the outer surface of the stent housing tube body 105 to treatment for increasing the lubricity of the outer surface. Examples of such treatment include a method of applying a coating, or fixing a hydrophilic polymer such as poly(hydroxyethyl methacrylate), poly(hydroxyethyl acrylate), hydroxypropyl cellulose, methyl vinyl ether maleic anhydride copolymer, polyethylene glycol, polyacrylamide, polyvinylpyrrolidone, and dimethylacrylamide-glycidyl methacrylate copolymer. Furthermore, the above-described material may be applied as a coating or fixed on the inner surface of the stent housing tube body 105 in order to improve the capability of sliding on the stent 103.

In addition, the stent housing tube body 105 may be formed by the combination of a two-layer structure of the above-described polymers (e.g., outer surface is nylon and inner surface is PTFE).

Furthermore, the stent delivery system 100 includes the pulling wire 106 whose one end is fixed to the proximal portion of the stent housing tube body 105. The pulling wire 106 goes beyond the proximal end of the stent housing tube body 105 and penetrates the slide tube 107 and the fixing tube 108 to extend in the proximal-side tube 104. In addition, the pulling wire 106 is pulled toward the proximal side of the proximal-side tube and thereby the stent housing tube body 105 and the slide tube 107 move toward the proximal side.

Moreover, as shown in FIG. 10, FIG. 11, FIGS. 15-18, and FIG. 20, in the stent delivery system 100, the plural (specifically, two) pulling wires 106a and 106b are included and the pulling wires 106a and 106b are fixed to the proximal portion of the stent housing tube body 105 by the fixture points 169a and 169b provided near the stent. Furthermore, the pulling wires 106a and 106b and these fixture points 169a and 169b are disposed so as to be separated by a predetermined distance.

In addition, in this embodiment, the pulling wires 106a and 106b are fixed to a member that moves by pulling. Specifically, as shown in FIG. 18 and as described above, the pulling wires 106a and 106b are fixed to the ring member 175 (specifically, an inner surface thereof) of the slide tube 107. Thus, in the stent delivery system 100 of this embodiment, the pulling wires 106a and 106b are pulled toward the proximal side and thus the ring member 175 is also pulled toward the proximal side. Furthermore, the slide tube 107 (slide tube main body 171) abuts on the ring member 175 and the slide tube is thus also pulled toward the proximal side. Therefore, in this embodiment, the stent housing tube body 105 and the slide tube 107 are pulled separately from each other and the stent housing tube body 105 does not abut on the slide tube 107 in pulling. Furthermore, the force in the pulling of the pulling wires 106a and 106b is dispersed to the fixture points 169a and 169b and fixture points 175a and 175b of the ring member 175, which is the member that moves when pulling. This reliably prevents release of the fixture between the pulling wires 106a and 106b and the stent housing tube body 105 at the fixture points 169a and 169b.

In the stent delivery system 100 of this embodiment, as shown in FIG. 10, the pulling wire 106 penetrates the proximal-side tube 104 and extends out beyond the proximal end of the proximal-side tube.

The constituent material for the pulling wire includes a single wire or a material obtained by twisting plural wires. Furthermore, the wire diameter of the pulling wire is normally 0.01 to 0.55 mm and particularly 0.1 to 0.3 mm is preferable, although it is not particularly limited.

Moreover, examples of the forming material of the pulling wire 106 include stainless steel wire (preferably, high-tensile stainless steel for spring), piano wire (preferably, piano wire plated with nickel or chromium), superelastic alloy wire, and wires formed by various kinds of metals such as Ni—Ti alloy, Cu—Zn alloy, Ni—Al alloy, tungsten, tungsten alloy, titanium, titanium alloy, cobalt alloy, and tantalum. In addition, the examples further include polymer materials with relatively high rigidity, such as polyamide, polyimide, ultra-high-molecular-weight polyethylene, polypropylene, and fluorine-based resin, and materials obtained by arbitrarily combining them.

Furthermore, the side surface of the pulling wire may be covered with a low friction resin to increase the lubricating ability. Examples of a low friction resin include fluorine-based resin, nylon 66, polyetheretherketone, and high density polyethylene, among which, the fluorine-based resin is more preferable. Examples of the fluorine-based resin include polytetrafluoroethylene, polyvinylidene fluoride, ethylene tetrafluoroethylene, and perfluoroalkoxy resin. Alternatively, coating with a silicon or various kinds of hydrophilic resins may be employed.

Moreover, in the stent delivery system 100 of this embodiment, a rigidity imparting body 111 is provided separately from the above-described pulling wire. As shown in FIGS. 10-13, FIG. 17, and FIG. 19, the rigidity imparting body 111 extends from the proximal side of stent delivery system 100 and passes through the proximal-side tube 104. Moreover, it enters the fixing tube 108. Furthermore, as shown in FIG. 19, a distal end 111a of the rigidity imparting body 111 is fixed to the slide tube locking portion 124. It is preferable to embed the distal end 111a of the rigidity imparting body 111 in the forming material of the slide tube locking portion 124 to thereby fix it. As shown in FIG. 12, the pulling wires 106a and 106b are not fixed to the slide tube locking portion 124 and pass through pathways 124a and 124b formed in the slide tube locking portion 124.

Moreover, in the stent delivery system 100 of this embodiment, as shown in FIG. 19, the rigidity imparting body 111 is fixed also to the tubular fixing member 184 fixed to the fixing tube 108. As shown in FIG. 19, a rigidity imparting body fixer 184a extending by a predetermined length along the axial direction is formed for the tubular fixing member 184. By fixing the distal portion of the rigidity imparting body 111 at two places in this manner, a strong reinforcement effect by the distal portion of the rigidity imparting body 111 is exerted. In particular, the slide tube locking portion 124 is reinforced when the slide tube 107 abuts on the slide tube locking portion 124.

Furthermore, it is preferable for the rigidity imparting body 111 to be fixed, at the proximal portion, to the proximal portion of the proximal-side tube 104 or the operation section 110 to be described later. Providing such a rigidity imparting body 111 can suppress deformation of the stent delivery system in pulling of the pulling member (pulling wire). In addition, the distal end 111a of the rigidity imparting body 111 may be so formed as to be a flat part in order to secure the fixture by the slide tube locking portion 124. Moreover, a stopper to prevent removal from the fixing member may be provided by forming a wave-like part in the side surface.

A single wire or a material obtained by twisting plural wires can be favorably used for the rigidity imparting body 111. Furthermore, the thickness of the rigidity imparting body 111 is preferably normally 0.01 to 1.5 mm and particularly 0.1 to 1.0 mm is preferable, although it is not particularly limited.

In addition, it is preferable for the rigidity imparting body 111 to be one in which the rigidity of the main-body-side portion (specifically, the portion in the proximal-side tube) is high (e.g. wire diameter is large) and the rigidity of the distal-side portion is low (specifically, the wire diameter is small). Moreover, it is preferable that the change point between both be a tapered part in which the wire diameter is changed in a tapered manner.

Furthermore, examples of the forming material of the rigidity imparting body 111 include stainless steel wire (preferably, high-tensile stainless steel for spring), piano wire (preferably, piano wire plated with nickel or chromium), superelastic alloy wire, and wires formed by various kinds of metals such as Ni—Ti alloy, Cu—Zn alloy, Ni—Al alloy, tungsten, tungsten alloy, titanium, titanium alloy, cobalt alloy, and tantalum. In addition, it is preferable for the rigidity imparting body 111 to be harder than the pulling member (pulling wire).

The stent 103 is housed in the stent housing tube body 105.

The stent 103 may be any known stent as long as it is a so-called self-expandable stent. The above-described stent 103 can be favorably used.

Figure 21:
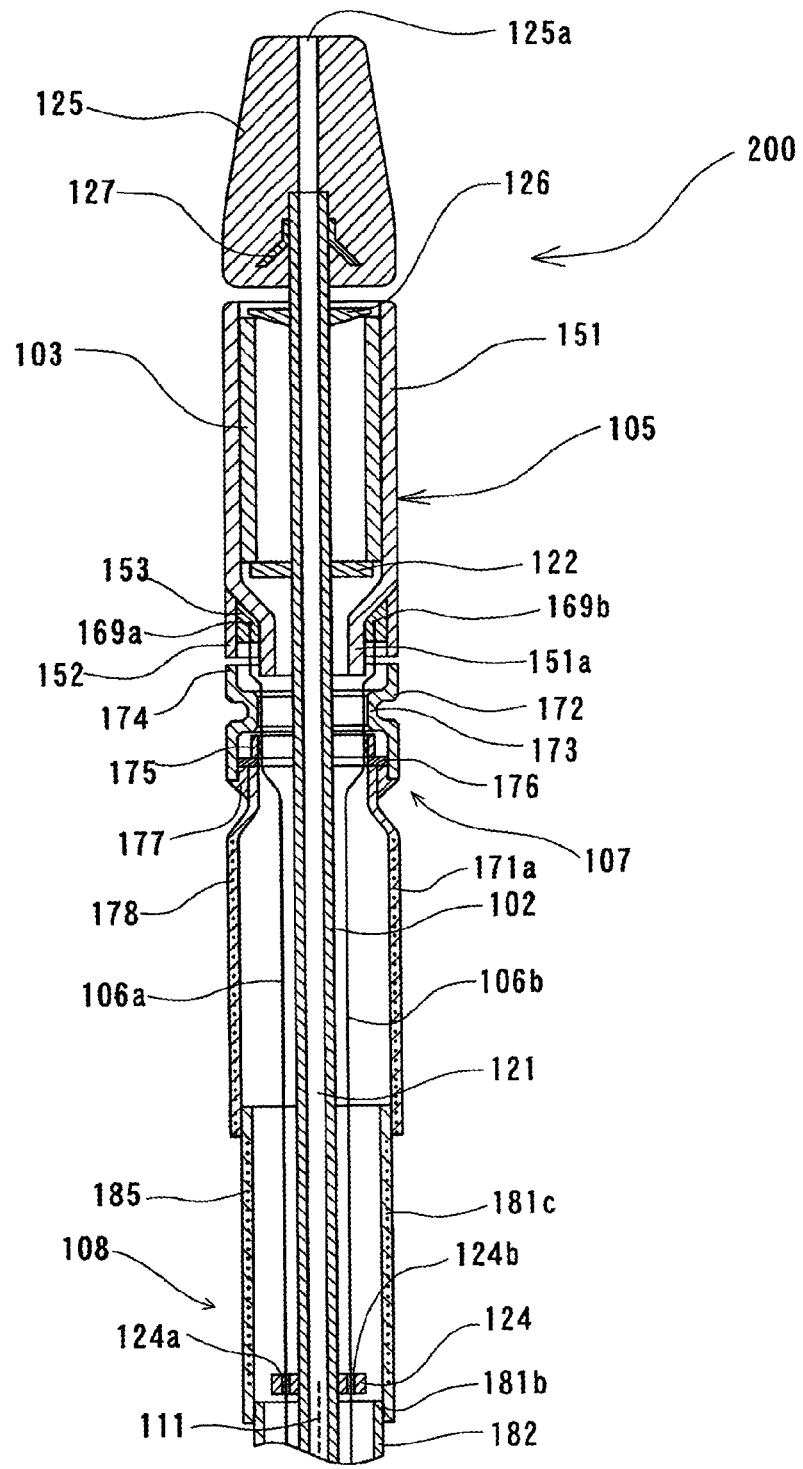
FIG. 21 is an enlarged sectional view of the distal portion of a stent delivery system according to a further embodiment disclosed here by way of example.

The stent delivery system according to a further embodiment disclosed here may be one like a stent delivery system 200 shown in FIG. 21.

In the stent delivery system of the above-described embodiment, the fixing tube 108 is of such a type as to house the slide tube 107 from the proximal side in pulling. In other words, the slide tube main body 171 of the slide tube 107 is of such a type as to enter the inside of the fixing tube 108 from the proximal end.

In contrast, in the stent delivery system 200 of this embodiment, the slide tube 107 is of such a type as to enclose the fixing tube 108 from the proximal side in pulling. In other words, a slide tube main body 171a of the slide tube 107 encloses a distal-side fixing tube 181c of the fixing tube 108 from the proximal end.

Therefore, the inner diameter of the slide tube main body 171a is almost equal to or slightly larger than the outer diameter of the distal-side fixing tube 181c of the fixing tube 108. The distal-side fixing tube 181c is fixed, at its proximal portion, to the distal portion of the proximal-side fixing tube 182 by the fixer 181b. Furthermore, in this embodiment, the portion 124 does not function as the slide tube locking portion.

Furthermore, as shown in FIG. 10 and FIGS. 22-26, the stent delivery system 100 of the present invention includes the operation section 110 fixed to the proximal end of the proximal-side tube 104.

Figure 22:
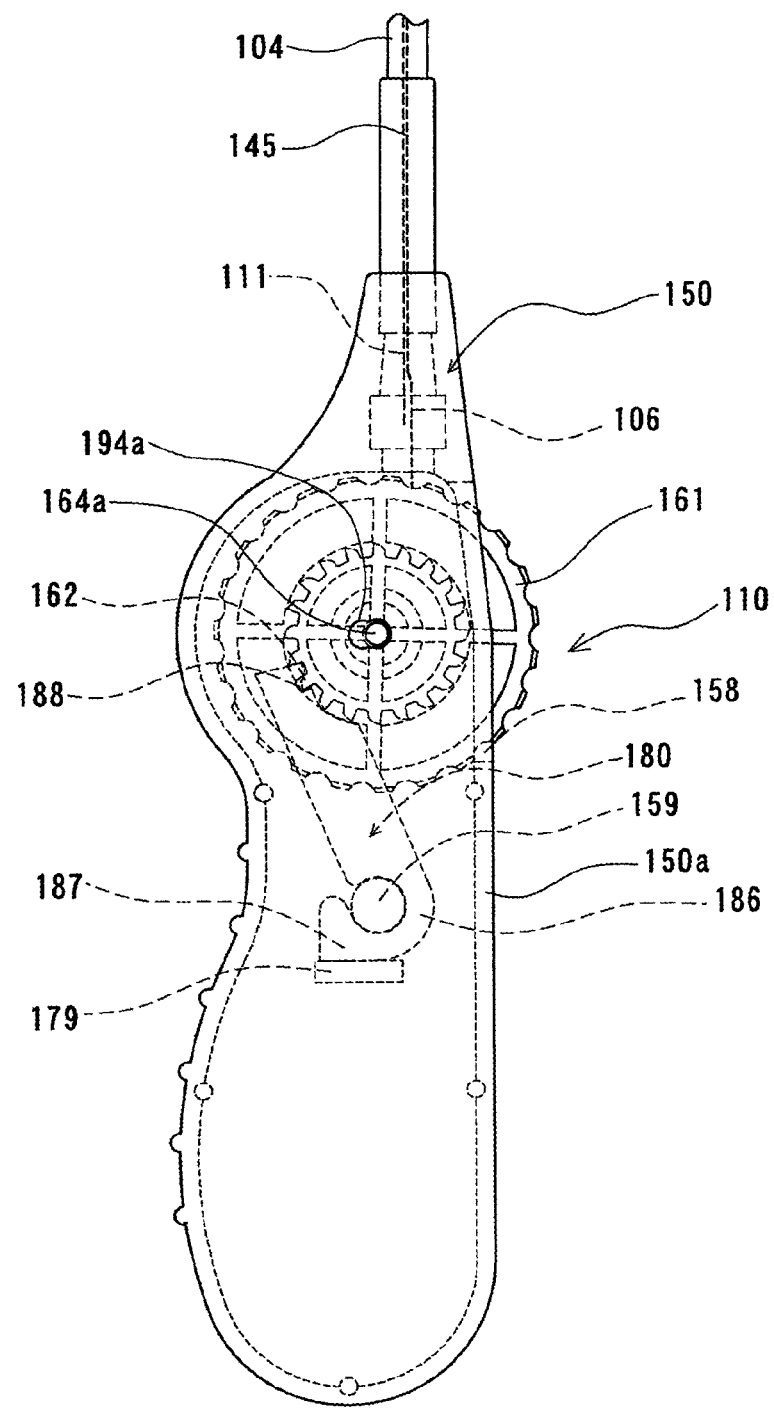
FIG. 22 is an enlarged front view in the vicinity of an operation section of the stent delivery system of FIG. 10.
Figure 23:
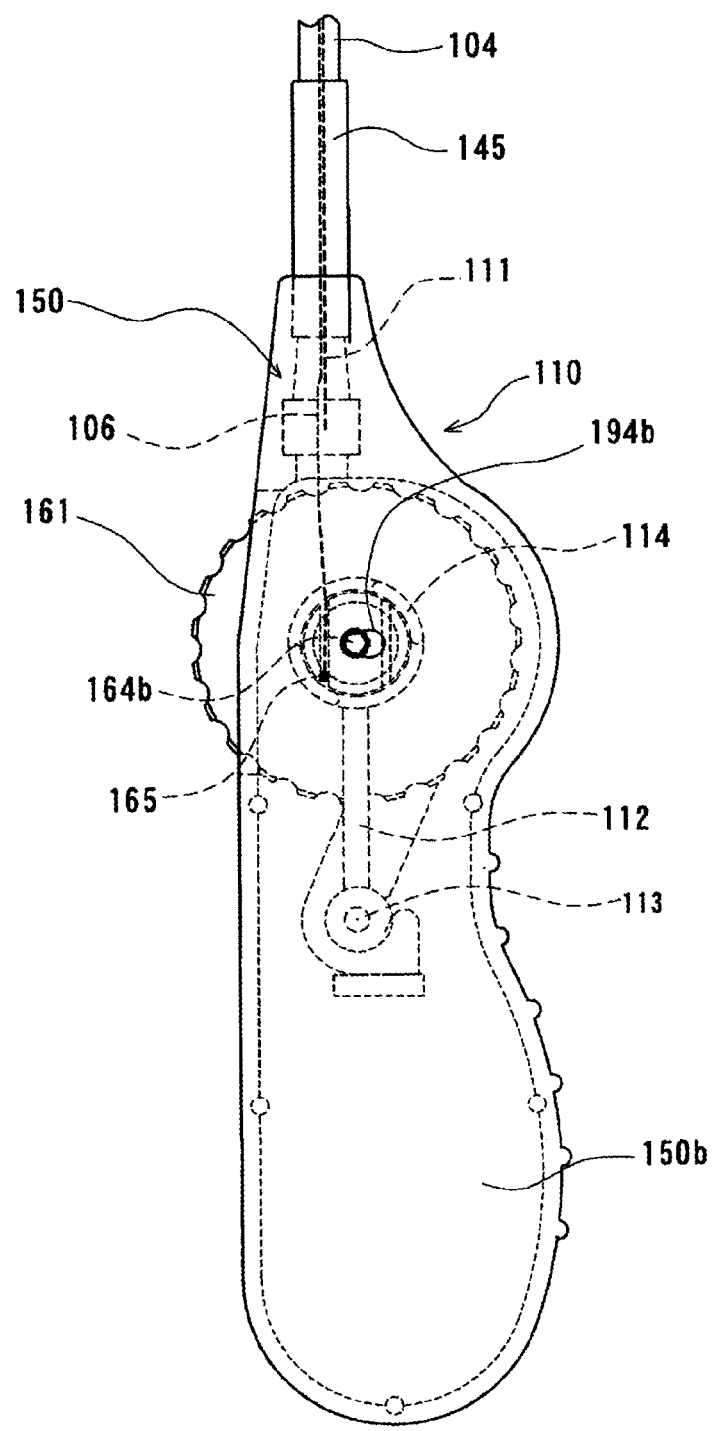
FIG. 23 is a back view in the vicinity of the operation section of the stent delivery system shown in FIG. 22.
Figure 24:
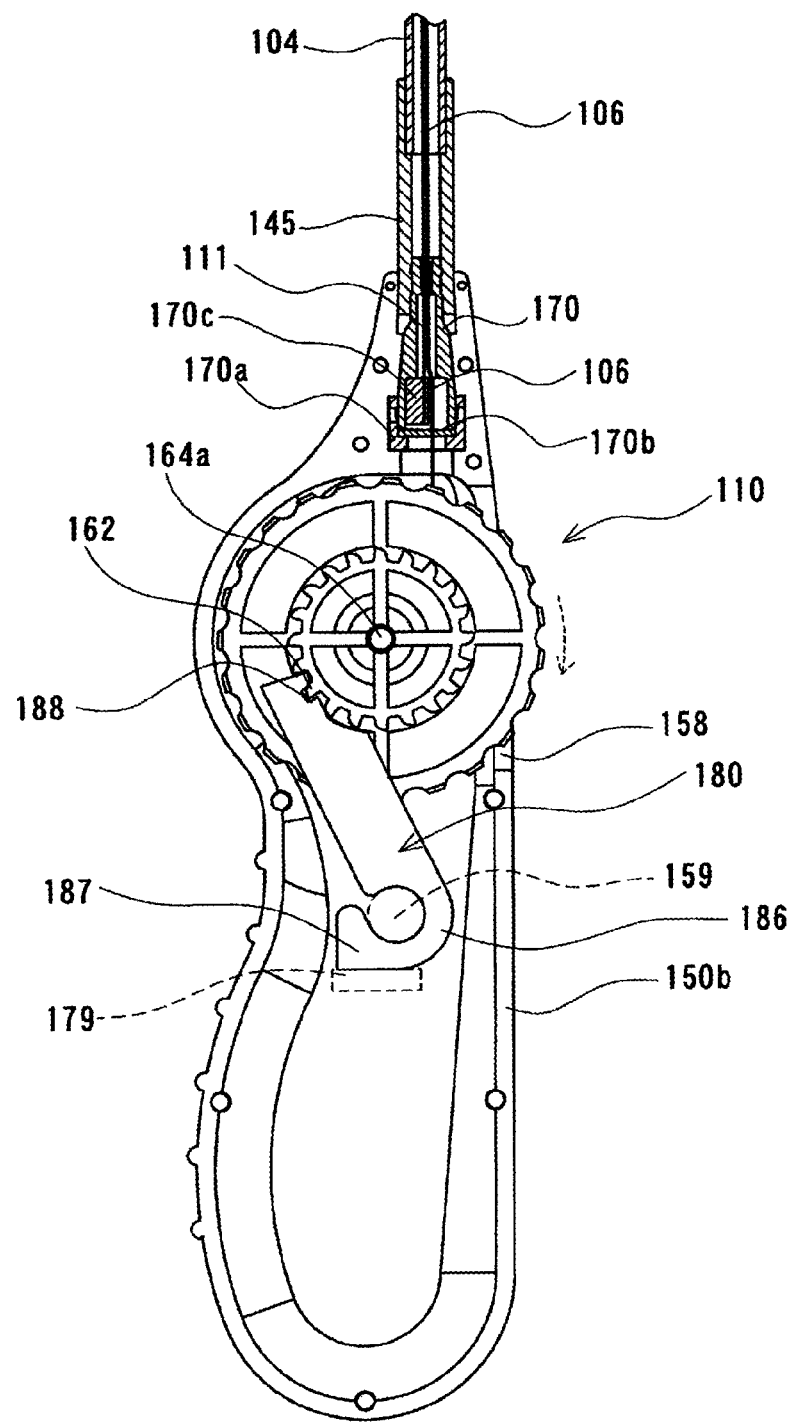
FIG. 24 is an explanatory diagram for explaining the internal structure of the operation section of the stent delivery system shown in FIG. 22.
Figure 25:
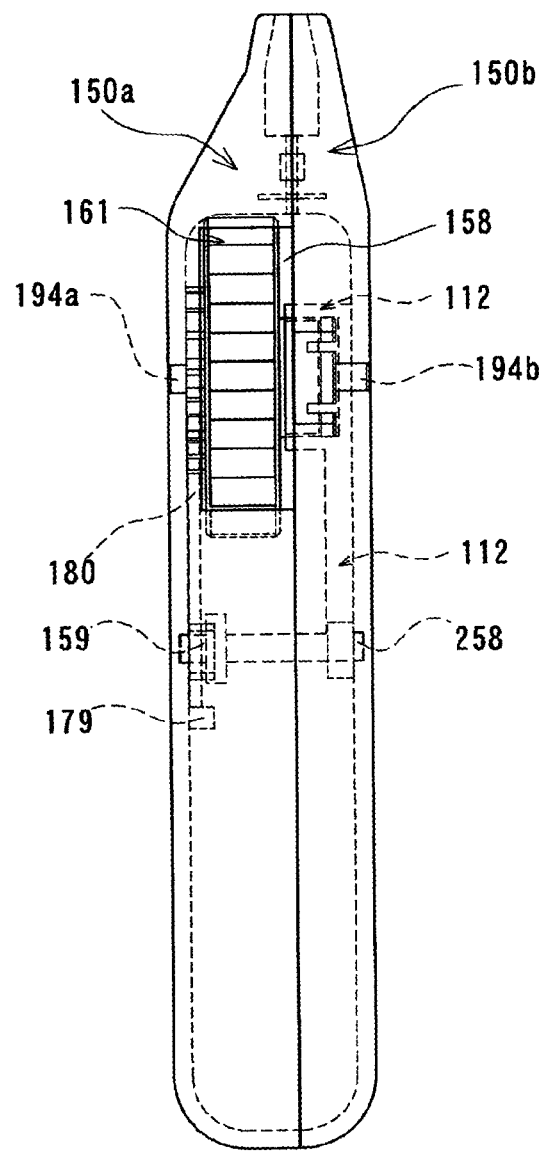
FIG. 25 is a right side view of only the operation section of the stent delivery system shown in FIG. 22.
Figure 26:
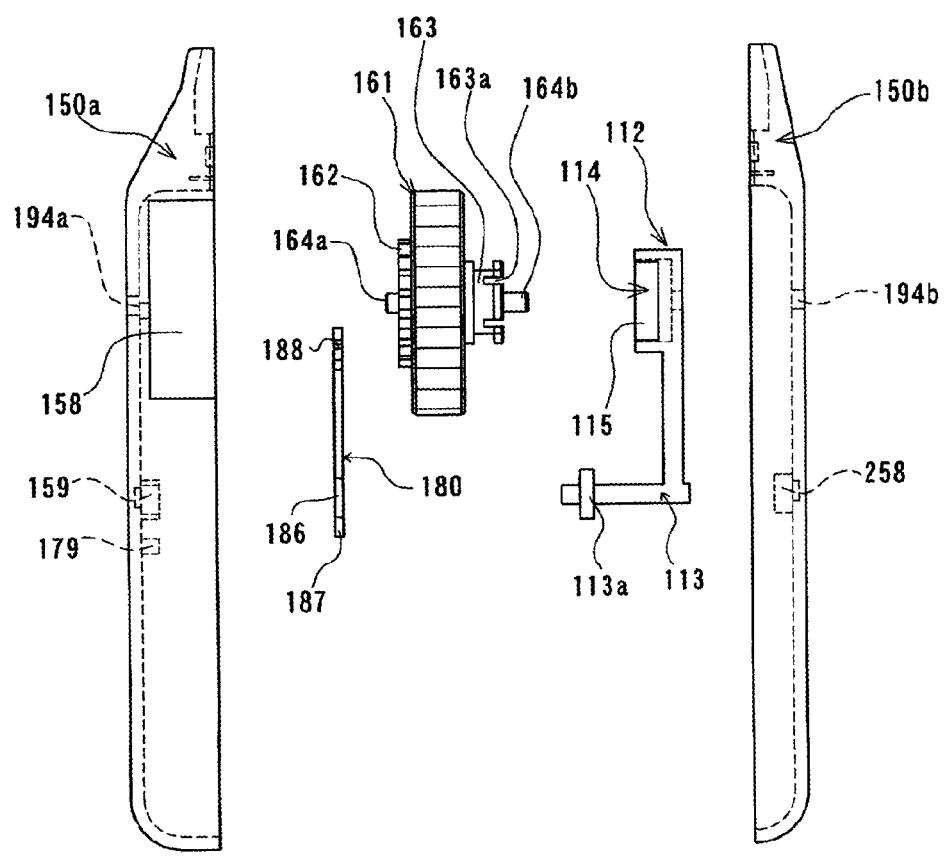
FIG. 26 is an explanatory diagram for explaining the internal structure of the operation section of the stent delivery system shown in FIG. 22.

FIG. 22 is an enlarged front view of the vicinity of the operation section of the stent delivery system of the disclosed embodiment, by way of example. FIG. 23 is a back view of the vicinity of the operation section of the stent delivery system shown in FIG. 22. FIG. 24 is an explanatory figure for explaining the internal structure of the operation section of the stent delivery system shown in FIG. 22. FIG. 25 is a right side view of only the operation section of the stent delivery system shown in FIG. 22. FIG. 26 is an explanatory figure for explaining the internal structure of the operation section of the stent delivery system shown in FIG. 22.

The operation section 110 in the stent delivery system 100 of this embodiment has, in addition to the pulling wire winding-up mechanism, a lock mechanism that releasably locks rotation of the pulling wire winding-up mechanism and a reverse rotation restriction mechanism that restricts rotation in the opposite direction to the pulling wire winding-up direction of the pulling wire winding-up function.

As shown in FIGS. 22-26, the operation section 110 includes an operation section housing 150. The operation section housing 150 is composed of a first housing 150a and a second housing 150b. The proximal side and center portion of the operation section housing 150 have a bent and rounded shape, which allows the operation section housing 150 to be easily grasped and facilitates roller operation in the grasped state.

Furthermore, as shown in FIG. 24, the distal part of a tubular connector 145 is fixed to the proximal end of the proximal-side tube 104. In addition, a seal mechanism connected to the proximal part of the connector 145 is housed in the operation section housing 150. As shown in FIG. 24, this seal mechanism includes a seal mechanism tubular main body member 170 having a distal part fixed to the proximal part of the connector 145, a cap member 170a fixed to the proximal end of the tubular main body member 170, a seal member 170b disposed between the tubular main body member 170 and the cap member 170a, and a rigidity imparting body fixing member 170c housed in the tubular main body member 170. The tubular main body member 170 and the cap member 170a have a penetrating opening. The seal member 170b has a hole part or slit for allowing the pulling wire 106 (106a, 106b) to penetrate in a liquid-tight manner and slidably. Furthermore, the proximal portion of the rigidity imparting body 111 is fixed to the rigidity giving body fixing member 170c. In addition, the rigidity giving body fixing member 170c is fixed in the tubular main body member 170.

As shown in FIGS. 22-25, the housing 150 has an opening 158 for allowing a rotary roller 161 to partially protrude for operation, a lock rib (not shown) that engages with a protrusion of a gear 162 provided for the roller 161, a bearing 194b that houses one end 164b of the rotary shaft of the roller 161, and a bearing 194a that houses the other end 164a of the rotary shaft of the roller 161. The lock rib has such a shape as to be capable of entering the space between the protrusions formed on the gear 162 of the roller 161. Furthermore, as shown in FIG. 22 and FIG. 23, the bearings 194a and 194b are "gourd-shaped" ones that house one end 164b and the other end 164a of the rotary shaft of the roller 161 and extend in such a direction as to be separated from the above-described opening. The bearings 194a and 194b are not limited to gourd-shaped ones, and any bearings that can move by such a distance so as to allow release of the engagement with the lock rib are acceptable. For example, the shape of the bearings 194a and 194b may be oblong, rectangular, elliptical, etc. In particular, in the operation section 110 of this embodiment, the above-described bearings 194a and 194b are gourd-shaped ones as shown in FIG. 22 and FIG. 23. Thus, by pushing the rotary roller 161 for operation to make the ends 164a and 164b of the rotary shaft of the roller 161 housed in the one-end-side spaces of the bearings 194a and 194b ride over rib parts that are formed on the inner surfaces of the center parts of the bearings 194a and 194b and face each other, the ends 164a and 164b of the rotary shaft of the roller 161 come to be housed in the other-end-side spaces of the bearings 194a and 194b. A state shown in FIG. 24 is the state in which the roller 161 is pressed. Furthermore, in this state, the roller 161 is pressed by a biasing member. However, the ends 164a and 164b of the rotary shaft of the roller 161 abut on the rib parts that are formed on the inner surfaces of the center parts of the bearings 194a and 194b and face each other, and thus do not move to the one-end-side spaces of the bearings 194a and 194b. Thus, the roller 161 keeps the rotatable state.

Furthermore, in this embodiment, as shown in FIG. 23 and FIG. 26, the operation section 110 includes a collar member 112. The collar member 112 has a collar part 114 that houses a winding-up shaft portion 163 and forms an annular space between the collar part 114 and the winding-up shaft portion 163. The collar part 114 prevents slack of the pulling wire wound up by the winding-up shaft portion 163. Furthermore, the collar member 112 also has a function to suppress induction of movement and backlash of the rotary roller when the rotary roller is pressed. A pin 113 of the collar member 112 is pivotally supported by a protrusion (bearing) 159 of the first housing 150a and a recess (bearing) 258 of the second housing 150b. Furthermore, as shown in FIG. 22 and FIG. 23, the bearings 194a and 194b are formed into a shape of a gentle circular arc around the pin 113 (bearings 159 and 258), and the roller 161 has such a length as to be capable of moving by a distance not lower than the height of the lock rib. In addition, as shown in FIG. 26, the collar member 112 has two notches 115 that reach the space in the collar part 114 from the side surface and face each other. The pulling wire 106 penetrates one notch 115 and is fixed to the winding-up shaft portion 163.

Furthermore, the pulling wire winding-up mechanism is defined by the roller 161 and the winding-up shaft portion 163, which rotates due to the rotation of this roller 161. The winding-up shaft portion 163 grasps or fixes the proximal portion of the pulling wire 106. Specifically, as shown in FIG. 23, the proximal portion of the pulling wire 106 is provided with an anchor part 165 that is formed so as to be larger than the wire 106 and a slit 163a capable of housing the pulling wire 106 is provided in the winding-up shaft portion 163. Furthermore, the proximal portion of the pulling wire 106 is housed in the slit 163a of the winding-up shaft portion 163 in such a manner that the anchor part 165 is located outside the proximal end of the slit 163a. Due to this arrangement, the wire 106 is wound up on the outer surface of the winding-up shaft portion 163 by the rotation of the winding-up shaft portion 163. The grasping or fixing of the pulling wire 106 to the winding-up shaft portion 163 is not limited to the above-described system and may be based on any system. For example, the proximal end or proximal portion of the pulling wire 106 may be fixed directly to the winding-up shaft.

Furthermore, it is preferable that the wound-up proximal portion of the pulling wire 106 be a flexible portion in order to facilitate the winding-up. Examples for providing such a flexible portion include forming the proximal portion of the pulling wire 106 from a flexible material and making the proximal portion of the pulling wire 106 have a small diameter.

Furthermore, in this embodiment, the winding-up shaft portion 163 is made integral with the rotary roller 161 coaxially with the rotary roller 161. Moreover, as shown in FIG. 26, the winding-up shaft portion 163 is provided on one side surface of the rotary roller 161. Furthermore, by rotating the rotary roller 161, the winding-up shaft portion 163 also rotates simultaneously. It is preferable that the amount of pulling wire wound-up be smaller than the amount of rotational operation of the rotary roller. This allows slow winding-up and also makes the movement of the stent housing tube body toward the proximal side slow and favorable. In this embodiment, the outer diameter of the winding-up shaft portion is smaller than the diameter of the roller for rotational operation. Therefore, the amount of winding-up of the pulling wire is smaller than the amount of rotational operation of the rotary roller.

Furthermore, the outer diameter of the winding-up shaft portion 163 is preferably 1 to 60 mm and, more particularly, 3 to 30 mm is preferable. The outer diameter of the rotary roller is preferably 1 to 20 times the outer diameter of the winding-up shaft portion and, more particularly, a diameter that is 1 to 10 times is preferable. In addition, the outer diameter of the rotary roller is preferably 10 to 60 mm and, more particularly, 15 to 50 mm is preferable.

The rotary roller and the winding-up shaft portion are not limited to the above-described integral embodiment, and the winding-up shaft portion may be one configured by a separate member that rotates in such a manner as to follow the rotation of the rotary roller. The system of transmission of the rotation of the rotary roller may be a gear-type one, belt-type one, etc. Furthermore, it is preferable that the surface part involving the possibility of contact in operating the roller 161 is a non-slippery surface. For example, it is preferable to perform a knurling treatment, embossing treatment, high friction material coating, or the like for the surface portion involving the possibility of contact in operating the roller 161.

Furthermore, the operation section 110 of this embodiment has the lock mechanism that releasably locks rotation of the pulling wire winding-up mechanism and the reverse rotation restriction mechanism that restricts rotation in the opposite direction to the pulling wire winding-up direction of the pulling wire winding-up function.

As shown in FIG. 24 and FIG. 26, the rotary roller 161 for operation has a gear 162 that is provided so as to rotate coaxially and integrally. In addition, as shown in FIG. 26, the gear 162 is provided on the other side surface of the rotary roller 161 (in other words, a surface on the opposite side to the surface on which the winding-up shaft portion 163 is provided). Thus, the gear 162 and the winding-up shaft portion 163 are in such a state as to be divided by the wall configured by the roller for operation.

Furthermore, the rotary roller 161 for operation is partially exposed from the opening and this part serves as the operation part. In addition, the rotary roller has the other end 164a of the rotary shaft provided on one side surface (specifically, side surface of the gear) and one end 164b of the rotary shaft provided on the other side surface (specifically, side surface of winding-up shaft).

Moreover, in the housing 150, biasing means (biasing member) 180 that biases the rotary roller 161 in the opening direction in the housing is provided. Specifically, the roller 161 is biased by the biasing means 180. Furthermore, the housing 150 is provided with a lock rib (not shown) capable of entering the space between protrusions of the gear 162 of the rotary roller 161 biased by the biasing member 180. Thus, in the state of being biased by the biasing member 180, the rotary roller 161 obtains the state shown in FIG. 23 and is incapable of rotation because the lock rib engages with the protrusion of the gear 162. Furthermore, if the rotary roller 161 is pushed in such a direction as to get separated from the lock rib, one end 164b and the other end 164a of the rotary shaft of the rotary roller move in the bearings 194a and 194b provided in the housing 150, so that the roller becomes rotatable. Accordingly, the operation section 110 of this embodiment has the lock mechanism that restricts rotation in the state in which the rotary roller 161 is not pressed and releasably locks rotation of the pulling wire winding-up mechanism.

Moreover, in the operation section of this embodiment, the reverse rotation restriction mechanism that restricts rotation in the opposite direction to the pulling wire winding-up direction of the pulling wire winding-up function is defined by the above-described biasing means 180 and the above-described gear 162.

As shown in FIGS. 22-24, the reverse rotation restriction mechanism is provided in the operation section 110. In this operation section 110, the reverse rotation restriction mechanism is provided for the biasing member 180 and the biasing member 180 serves also as a reverse rotation restriction member. The reverse rotation restriction mechanism includes a mesh part 188 that is provided at the part facing the gear 162 of the above-described rotary roller 161 for operation at the distal part of the reverse rotation restriction member (serving also as biasing member) 180 and is capable of meshing with the gear. The reverse rotation restriction mechanism further includes an elastically deformable part 186 and a mounting part 187 to the housing. Furthermore, the first housing 150a has the first protrusion (bearing) 159 and a second protrusion 179 formed on the inner surface. The first protrusion 159 enters the inside of the elastically deformable part 186 of the reverse rotation restriction member (biasing member) 180 and has an outer surface shape corresponding to the inner surface shape of the elastically deformable part 186. Specifically, the inner surface shape of the elastically deformable part 186 is a circular arc shape and the first protrusion 159 has a cylindrical shape corresponding to this circular arc shape. Furthermore, the mounting part 187 of the reverse rotation restriction member (biasing member) 180 has such a shape as to be mountable between the first protrusion 159 and the second protrusion 179 formed on the first housing 150a. Moreover, the reverse rotation restriction member (biasing member) 180 is mounted so as to be incapable of rotation due to the mounting of its mounting part 187 between the first protrusion 159 and the second protrusion 179 of the first housing 150a. In addition, the reverse rotation restriction member (biasing member) 180 biases the rotary roller 161 for operation in the direction of the opening 158 by the elastic force of the elastically deformable part 186. Furthermore, the movement of the mounting part 187 of the reverse rotation restriction member (biasing member) 180 in the side surface direction is restricted by a disc-like protrusion 113a provided on the collar member 112.

Moreover, as described above, by pressing the roller 161, the roller becomes rotatable. However, although rotation in the arrow direction in FIG. 24 (direction to winding up the pulling wire) is possible, if rotation of the roller 161 in the opposite direction is attempted, one tooth of the gear 162 engages with the mesh part 188 of the reverse rotation restriction member (biasing member) 180, which restricts this rotation. This restricts the rotation of the roller in the opposite direction to the pulling wire winding-up direction of the pulling wire winding-up function. Furthermore, in this operation section 110, as shown in FIG. 25, the reverse rotation restriction member (biasing member) 180 is disposed between the inner surface of the first housing 150a and the side surface of the rotary roller 161. Therefore, motion of the reverse rotation restriction member (biasing member) 180 in the lateral direction (horizontal direction) is restricted by the inner surface of the first housing 150a and the side surface of the rotary roller 161.

The gear 162 is one having a diameter smaller than that of the rotary roller. The outer diameter of the gear 162 is preferably 10 to 60 mm and, more particularly, 15 to 50 mm is preferable. The number of teeth on the gear 162 is preferably 4 to 200 and, more preferably, 4 to 70.

Furthermore, one end of the collar member 112 included in the operation section 110 is pivotally supported by the pin 113 and the collar part 114 on the other end side houses the winding-up shaft portion 163 and forms an annular space between the collar part 114 and the winding-up shaft portion 163. This annular space is not a very large space and a small annular space is formed between the collar part 114 and the outer surface of the wound-up wire.

Next, a method for using the stent delivery system 100 of the disclosed embodiment will be described with reference to the accompanying drawings.

First, the proximal portion of a guidewire is inserted into the opening 125a of the distal-end member of the stent delivery system shown in FIG. 10 and FIG. 11 and the guidewire (not shown) is led out from the opening 123. Next, the stent delivery system 100 is inserted into a guiding catheter (not shown) inserted in a living body, and the stent delivery system 100 is pushed forward along the guidewire to locate the stent housing portion of the stent housing tube body 105 in the intended stenosis.

Next, the rotary roller 161 for operation in the operation section 110 is pressed and thereafter the roller is rotated in the arrow direction in FIG. 24. Thereby, the pulling wire 106 is wound up on the outer circumferential surface of the winding-up shaft 163. In addition, the stent housing tube body 105 and the slide tube 107 move toward the proximal side along the axial direction. At this time, the proximal-end surface of the stent 103 abuts on the distal-end surface of the stent proximal part locking portion 122 of the distal-side tube 102 and the stent 103 is locked. Thus, in association with the movement of the stent housing tube body 105, the stent 103 is discharged from the distal-end opening of the stent housing tube body 105. Due to this discharge, the stent 103 is self-expanded to expand the stenosis and is indwelled in the stenosis as shown in FIG. 20.

The detailed description above describes features and aspects of examples of embodiments of a stent delivery system. The present invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent delivery system comprising:
a stent formed into a substantially cylindrical shape,
an inner tube body having a guidewire lumen, and
a stent housing tube body that houses the stent in a distal portion,
wherein the stent is configured to be compressed in a center axis direction when being inserted into a living body and expanded outward to be restored to a shape before compression when being indwelled in a living body,
wherein the stent is disposed so as to cover a distal portion of the inner tube body, the stent being discharged by moving the stent housing tube body toward a proximal side relative to the inner tube body,
wherein an inner surface of the stent housing tube body from at least a distal end of the stent housing tube body to a proximal part of a stent housing portion is a substantially polygonal prism inner surface extending along an axial direction of the stent housing tube body.

2. The stent delivery system as defined in claim 1, wherein the substantially polygonal prism inner surface has substantially no bent part.

3. The stent delivery system as defined in claim 1, wherein the substantially polygonal prism inner surface extends in parallel with the axial direction of the stent housing tube body.

4. The stent delivery system as defined in claim 1, wherein the substantially polygonal prism inner surface defines a gentle helical shape with respect to the axial direction of the stent housing tube body.

5. The stent delivery system as defined in claim 1,
wherein the inner tube body includes a distal-side tube including the guidewire lumen, a proximal-side tube, and a fixing tube to which a proximal portion of the distal-side tube and a distal portion of the proximal-side tube are fixed and that has an opening communicating with the guidewire lumen,
wherein the stent housing tube body encloses a distal side of the distal-side tube and is slidable in the proximal direction of the distal-side tube, and further comprising:
at least one pulling wire having one end fixed to the stent housing tube body and extending in the proximal-side tube, the pulling wire configured to move the stent housing tube body toward the proximal side by pulling the pulling wire toward a proximal side of the proximal-side tube.

6. The stent delivery system as defined in claim 5, wherein the distal-side tube has a stent proximal part locking portion located on the distal side of the distal-side tube, and the stent proximal part locking portion abuts on a proximal end of the stent housed in the stent housing tube body such that the stent proximal part locking portion restricts movement of the stent toward the proximal side.

7. The stent delivery system as defined in claim 5, further comprising a slide tube disposed close to a proximal end of the stent housing tube body, wherein the fixing tube is configured for housing the slide tube from the proximal side or for encasing the slide tube from the proximal side, wherein the slide tube is configured to move toward the proximal side together with the stent housing tube body upon pulling of the pulling wire and the slide tube is not fixed to the stent housing tube body.

8. The stent delivery system as defined in claim 5, further comprising an operation section provided at a proximal portion of the proximal-side tube, the operation section including a pulling wire winding-up mechanism for winding up the pulling wire to move the stent housing tube body toward the proximal side.

9. The stent delivery system as defined in claim 1, wherein the substantially polygonal prism inner surface includes a plurality of angled inner surfaces portions, adjacent angled inner surface portions intersecting at a corner.

10. The stent delivery system as defined in claim 1, wherein the stent includes a plurality of annular bodies connected by a plurality of connecting portions, at least some of the connecting portions defining circular connecting portions configured to retain a radiopaque marker.

11. A stent delivery system comprising:
a stent formed into a substantially cylindrical original shape,
a sheath that houses the stent in a distal portion,
wherein the stent is configured to be compressed in a center axis direction when being inserted into a living body and expanded outward to be restored to the substantially cylindrical original shape before compression when being indwelled in a living body,
wherein an inner surface of the sheath defines a substantially polygonal prism inner surface extending along an axial direction of the sheath.

12. The stent delivery system as defined in claim 11, wherein the substantially polygonal prism inner surface extends in parallel with the axial direction of the sheath.

13. The stent delivery system as defined in claim 11, wherein the substantially polygonal prism inner surface defines a gentle helical shape with respect to the axial direction of the sheath.

14. The stent delivery system as defined in claim 11, wherein the substantially polygonal prism inner surface includes a plurality of angled inner surfaces portions, adjacent angled inner surface portions intersecting at a corner.

15. The stent delivery system as defined in claim 11, further comprising an inner tube having a guidewire lumen, wherein the stent is disposed so as to cover a distal portion of the inner tube, the stent being discharged by moving the sheath toward a proximal side relative to the inner tube.

16. The stent delivery system as defined in claim 15,
wherein the inner tube includes a distal-side tube including the guidewire lumen, a proximal-side tube, and a fixing tube to which a proximal portion of the distal-side tube and a distal portion of the proximal-side tube are fixed and that has an opening communicating with the guidewire lumen,
wherein the sheath encloses a distal side of the distal-side tube and is slidable in the proximal direction of the distal-side tube, and further comprising:
at least one pulling wire having one end fixed to the sheath and extending in the proximal-side tube, the pulling wire configured to move the sheath toward the proximal side by pulling the pulling wire toward a proximal side of the proximal-side tube.

17. The stent delivery system as defined in claim 16, wherein the distal-side tube has a stent proximal part locking portion located on the distal side of the distal-side tube, and the stent proximal part locking portion abuts on a proximal end of the stent housed in the sheath such that the stent proximal part locking portion restricts movement of the stent toward the proximal side.

18. The stent delivery system as defined in claim 16, further comprising a slide tube disposed close to a proximal end of the sheath, wherein the fixing tube is configured for housing the slide tube from the proximal side, wherein the slide tube is configured to move toward the proximal side together with the sheath upon pulling of the pulling wire and the slide tube is not fixed to the sheath.

19. The stent delivery system as defined in claim 16, further comprising an operation section provided at a proximal portion of the proximal-side tube, the operation section including a pulling wire winding-up mechanism for winding up the pulling wire to move the sheath toward the proximal side.

20. A method for indwelling a stent in a target stenosis of a living body comprising:
providing a stent delivery system comprising a stent formed into a substantially cylindrical original shape, an inner tube body having a guidewire lumen, and a stent housing tube body that houses the stent in a distal portion, wherein the stent is configured to be compressed in a center axis direction when being inserted into the living body and expanded outward to be restored to the original shape when being indwelled in the living body, wherein the stent is disposed so as to cover a distal portion of the inner tube body, wherein at least a portion of an inner surface of the stent housing tube body is a substantially polygonal prism inner surface extending along an axial direction of the stent housing tube body, wherein the inner tube body includes a distal-side tube including the guidewire lumen, a proximal-side tube, and a fixing tube to which a proximal portion of the distal-side tube and a distal portion of the proximal-side tube are fixed and that has an opening communicating with the guidewire lumen, wherein the stent housing tube body encloses a distal side of the distal-side tube and is slidable in a proximal direction of the distal-side tube, and at least one pulling wire having one end fixed to the stent housing tube body and extending in the proximal-side tube, the pulling wire configured to move the stent housing tube body toward the proximal side by pulling the pulling wire toward a proximal side of the proximal-side tube,
inserting a proximal portion of a guidewire into a distal opening of the distal-side tube of the stent delivery system and leading the guidewire out through the opening in the fixing tube,
inserting the stent delivery system into a guiding catheter inserted in the living body,
pushing the stent delivery system forward along the guidewire to locate a stent housing portion of the stent housing tube body at the target stenosis,
pulling the pulling wire such that the stent housing tube body and a slide tube disposed close to a proximal end of the stent housing tube body move toward a proximal side,
abutting a proximal-end surface of the stent on a distal-end surface of a stent proximal part locking portion of the distal-side tube such that the stent is locked,
discharging the stent from a distal-end opening of the stent housing tube body,
self-expanding the stent at the target stenosis to thereby indwell the stent and expand the stenosis.

* * * * *